United States Patent
Mondiere et al.

(10) Patent No.: US 10,207,985 B2
(45) Date of Patent: Feb. 19, 2019

(54) COMPOUNDS

(71) Applicant: SYNGENTA PARTICIPATIONS AG, Basel (CH)

(72) Inventors: Regis Jean Georges Mondiere, Stein (CH); Olivier Loiseleur, Stein (CH); Andre Jeanguenat, Stein (CH); Anthony Cornelius O'Sulivan, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 14/908,239

(22) PCT Filed: Aug. 8, 2014

(86) PCT No.: PCT/EP2014/067057
§ 371 (c)(1),
(2) Date: Jan. 28, 2016

(87) PCT Pub. No.: WO2015/022265
PCT Pub. Date: Feb. 19, 2015

(65) Prior Publication Data
US 2016/0176806 A1   Jun. 23, 2016

(30) Foreign Application Priority Data

Aug. 13, 2013  (EP) .................... 13180287
Aug. 13, 2013  (EP) .................... 13180288

(51) Int. Cl.

| | | |
|---|---|---|
| C07C 233/65 | (2006.01) | |
| C07D 215/48 | (2006.01) | |
| C07D 317/62 | (2006.01) | |
| C07D 231/16 | (2006.01) | |
| C07D 231/56 | (2006.01) | |
| C07D 333/38 | (2006.01) | |
| C07D 333/72 | (2006.01) | |
| C07D 401/12 | (2006.01) | |
| C07D 405/04 | (2006.01) | |
| C07D 409/12 | (2006.01) | |
| C07D 239/557 | (2006.01) | |
| C07D 277/32 | (2006.01) | |
| C07D 277/64 | (2006.01) | |
| C07D 209/42 | (2006.01) | |
| C07D 213/38 | (2006.01) | |
| C07D 307/82 | (2006.01) | |
| A01N 37/18 | (2006.01) | |
| A01N 43/10 | (2006.01) | |
| A01N 43/40 | (2006.01) | |
| C07C 233/06 | (2006.01) | |
| C07D 213/06 | (2006.01) | |
| C07D 333/20 | (2006.01) | |
| C07D 333/58 | (2006.01) | |

(52) U.S. Cl.
CPC ............ *C07C 233/65* (2013.01); *A01N 37/18* (2013.01); *A01N 43/10* (2013.01); *A01N 43/40* (2013.01); *C07C 233/06* (2013.01); *C07D 209/42* (2013.01); *C07D 213/06* (2013.01); *C07D 213/38* (2013.01); *C07D 215/48* (2013.01); *C07D 231/16* (2013.01); *C07D 231/56* (2013.01); *C07D 239/557* (2013.01); *C07D 277/32* (2013.01); *C07D 277/64* (2013.01); *C07D 307/82* (2013.01); *C07D 317/62* (2013.01); *C07D 333/20* (2013.01); *C07D 333/38* (2013.01); *C07D 333/58* (2013.01); *C07D 333/72* (2013.01); *C07D 401/12* (2013.01); *C07D 405/04* (2013.01); *C07D 409/12* (2013.01)

(58) Field of Classification Search
CPC ............... C07C 233/65; C07D 21/48
See application file for complete search history.

(56) References Cited

FOREIGN PATENT DOCUMENTS

| | | |
|---|---|---|
| EP | 1591442 A1 | 11/2005 |
| WO | 2006122955 A1 | 11/2006 |
| WO | 2013064460 A1 | 5/2013 |
| WO | 2013143811 A1 | 10/2013 |

OTHER PUBLICATIONS

International Search Report for PCT/EP2014/067057, dated Feb. 18, 2015.

*Primary Examiner* — Craig D Ricci
*Assistant Examiner* — Christopher R Stone

(57) ABSTRACT

Compounds of the formula in which the substituents are as defined in claim 1, are suitable for use as nematicides.

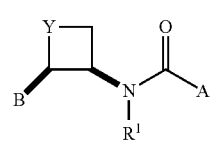

(I)

8 Claims, No Drawings

COMPOUNDS

RELATED APPLICATION INFORMATION

This application is a 371 of International Application No. PCT/EP2014/067057, filed Aug. 8, 2014, which claims priority to European Patent Application No. 13180287.8, filed Aug. 13, 2013, and European Patent Application No. 13180288.6, filed Aug. 13, 2013, the contents of all of which are incorporated herein by reference herein.

The present invention relates to novel four membered ring carboxamide compounds, a process for the preparation of these compounds and their use as nematicides.

Cyclobutylcarboxamides are described, for example, in WO 09/043784, WO06/122952, WO06/122955, WO05/103006, WO05/103004 and WO04/014842.

Novel four membered ring carboxamides have now been found characterized by a cis substituted four membered ring, which show good nematicidal activity.

The present invention thus relates to compounds of the formula I

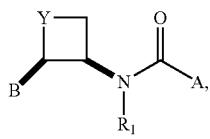

(I)

wherein

Y is O or CH2;

A represents phenyl or a 5- or 6-membered heteroaromatic ring containing 1 to 3 heteroatoms independently selected from oxygen, nitrogen and sulphur, wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur optionally substituted by one or more R4;

R1 represents hydrogen, hydroxy, C1-C4-alkyl, C1-C4-alkoxy, C1-C4-alkylcarbonyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl;

each R2 independently of one another represents halogen, cyano, C1-C4-alkyl, C1-C4-haloalkyl, C1-C4-alkoxy, C1-C4-haloalkoxy or C1-C4-haloalkylthio;

each R3 independently of one another represents halogen, cyano, C1-C4-alkyl, C3-C4 cycloalkyl, C1-C4-haloalkyl, C1-C4-alkoxy, C1-C4-haloalkoxy or C1-C4-haloalkylthio;

each R4 independently of one another represents halogen, cyano, C1-C4-alkyl, C1-C4-haloalkyl, C1-C4-alkoxy, C1-C4-haloalkoxy, C2-C6-haloalkenyl, C2-C6 haloalkynyl or C3-C6-cycloalkyl optionally substituted by one or more substituents R5;

each R5 independently of one another represents halogen, cyano, C1-C4-alkyl or C1-C4-haloalkyl;

wherein B and A-CO—NR1 are cis to each other on the four-membered ring, and tautomers/isomers/enantiomers or N-oxides of these compounds.

In the substituent definitions of the compounds of the formula I, each alkyl moiety either alone or as part of a larger group (such as alkoxy, alkylthio, alkoxycarbonyl and alkylcarbonyl) is a straight or branched chain and is, for example, methyl, ethyl, n-propyl, n-butyl, isopropyl, sec-butyl, isobutyl, tert-butyl, pentyl, iso-pentyl or n-hexyl. The alkyl groups are suitably C1-C4-alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. Preferably, the alkenyl and alkynyl moieties contain 2 to 6, more preferably 3 or 4 carbon atoms.

Halogen is fluorine, chlorine, bromine or iodine, preferably fluorine, chlorine or bromine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

Cycloalkyl includes cyclopropyl, cyclobutyl, cyclopentyl and cyclohexyl. Cycloalkyl is preferably cyclopropyl or cyclobutyl.

The term "heteroaryl", "heteroaromatic ring" or "heteroaromatic ring system" refers to aromatic ring systems containing at least one heteroatom and consisting either of a single ring or of two fused rings. Preferably, single rings will contain up to 3 and bicyclic systems up to 5 heteroatoms, which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl.

Compounds of the formula (I) can occur in at least two enantiomeric forms: (Iaa) and (Iab). B and A-CO—NR1 are cis to each other in each of these enantiomers (Iaa) and (Iab). Wedged bonds shown for example in the compounds of formula (Iaa) and (Iab) represent absolute stereochemistry, whereas thick straight bonds such as those shown for the compounds of formula (I) represent relative stereochemistry in racemic compounds. This applies throughout. The difference between (Iaa) and (Iab) is that the two carbon atoms bearing the B and the A-CO—NR1 groups each have their absolute stereochemistry formally inverted.

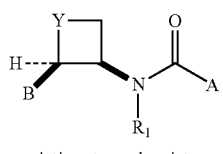

(I)

relative stereochemistry

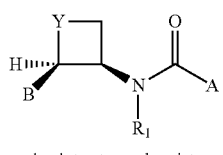

(Iaa)

absolute stereochemistry

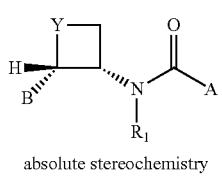

(Iab)

absolute stereochemistry

A racemic compound (I) is a 1:1 mixture of the compounds of formula (Iaa) and (Iab). Other ratios of (Iaa) and (Iab) are possible and part of the present invention. Examples of such ratios of (Iaa) to (Iab) are 1:99, 2:98, 5:95, 10:90, 20:80, 30:70; 40:60, 45:55; 55:45; 60;40, 70:30, 80:20, 90:10, 95:5, 98;2, and 99:1. In a preferred embodiment, the weight ratio of (Iaa) to (Iab) is weighted towards compound of formula (Iab), for example, the ratio of (Iaa) to (Iab) being 1:99, 2:98, 5:95, 10:90, 20:80, 30:70; 40:60, or 45:55. In a more preferred embodiment, the compound of formula (I) consists essentially of the compound of formula (Iab); even more preferably, the compound of formula (I) is the compound of formula (Iab). This also applies to each relevant intermediate described herein therefor and the relevant enantiomer.

The trans isomers of compounds of formula (I), wherein B and A-CO—NR1 are trans to each other on the four-membered ring, can be formed as side products in the synthesis of compounds of the formula (I). Mixtures containing up to 50%, preferably up to 40%, more preferably up to 30%, especially up to 20%, advantageously up to 10%, desirably up to 5%, in particular up to 3%, of the trans isomer are understood to be also part of this invention, such as any one of compounds of formulae (I) and (Iab) and each relevant intermediate described herein therefor.

Preferably, the ratio of the compound of formula (I) to its trans isomer is greater than 1.5:1, more preferably greater than 2.5:1, especially greater than 4:1, advantageously greater than 9:1, desirably greater than 20:1, in particular greater than 35:1.

It is possible that compounds of the formula (I) have further stereochemical centres in one or more of the substituents. Further isomers are then possible. The invention covers all such isomers and mixtures thereof.

The compounds of the formula (I) may occur in different tautomeric forms. The invention covers all those tautomeric forms and mixtures thereof.

The following list provides definitions, including preferred definitions, for substituents Y, A, B, R1, R2, R3, R4 and R5 with reference to compounds of formula (I). These definitions also apply in particular to the compound of formula (Iab). For any one of these substituents, any of the definitions given below may be combined with any definition of any other substituent given below or elsewhere in this document.

Y represents O or CH2.

Preferably, Y represents CH2.

A represents phenyl or a 5- or 6-membered heteroaromatic ring containing 1 to 3 heteroatoms independently selected from oxygen, nitrogen and sulphur, wherein the phenyl is optionally substituted by one or more R2 and the heteroaromatic ring is optionally substituted by one or more R3.

Preferably, A represents phenyl, pyridyl, pyrimidyl, pyrazinyl, pyrazolyl, thienyl or furyl, wherein the phenyl is optionally substituted by one or more R2 and the heteroaromatic ring is optionally substituted by one or more R3.

More preferably, A represents phenyl, pyridyl, pyrazinyl or pyrazolyl wherein the phenyl is optionally substituted by one or more R2 and the heteroaromatic ring is optionally substituted by one or more R3.

Most preferably, A represents phenyl optionally substituted by one R2, 2-pyrazinyl, 2-pyridyl or 3-pyridyl wherein the pyrazinyl and pyridyl are optionally substituted by one R3.

Preferably, in the embodiments described above, A represents 2-pyridyl, 3-pyridyl, 2-pyrimidyl, 4-pyrimidyl, 2-pyrazinyl, 4-pyrazolyl, 2-thienyl, 3-thienyl, 2-furyl or 3-furyl, as may be appropriate.

In an instance, there are 1 to 3 substituents R2 or R3 on A. Preferably, A is substituted by one or two of such substituents, most preferably, A is substituted by one substituent R2 or R3. The preferable point or points of attachment of these substituents is ortho to the point of attachment of A to C(O)NR1.

B represents a mono- or bicyclic 5 to 10 membered heteroaromatic ring system containing 1 to 5 heteroatoms, each independently selected from oxygen, nitrogen and sulphur, optionally substituted by one or more R4.

Preferably, B represents pyridyl, pyrazinyl, pyridazinyl, pyrimidinyl, thienyl, pyrazolyl, thiazolyl, benzothiazolyl, benzoimidazolyl, quinolinyl or imidazopyridinyl, each optionally substituted by one or more R4.

More preferably, B represents pyridyl, pyrazinyl, pyridazinyl, pyrimidinyl, thienyl, pyrazolyl, thiazolyl, benzothiazolyl, benzoimidazolyl or imidazopyridinyl, each optionally substituted by one or more R4.

Even more preferably, B represents pyridyl, pyrazinyl, pyridazinyl, pyrimidinyl, thienyl, pyrazolyl, thiazolyl, benzothiazolyl, benzoimidazolyl, imidazo[4,5 b]pyridinyl or imidazo[4,5 c]pyridinyl, each optionally substituted by one or more R4.

More preferably again, B represents pyridyl, pyrazinyl, pyrimidinyl, thienyl, pyrazolyl, thiazolyl, 2-benzothiazolyl, 2-benzoimidazolyl, 2-imidazo[4,5 b]pyridinyl or 2-imidazo [4,5 c]pyridinyl, each optionally substituted by one or more R4.

Yet more preferably, B represents pyridyl, thienyl or pyrazolyl, each optionally substituted by one or more R4.

Yet more preferably again, B represents 2-pyridyl, 3-pyridyl, 2-thienyl, 3-thienyl or 4-pyrazolyl, each optionally substituted by one or more R4.

B is preferably substituted by 1 to 3 substituents R4, more preferably 1 or 2 substituents R4. The preferable point or points of attachment of these substituents is para to the point of attachment of B to the four-membered ring when B is substituted by 1 substituent R4 or para and ortho to the point of attachment of B to the four-membered ring when B is substituted by 2 or 3 substituents R4. When B is pyridyl, pyrazinyl or pyrimidinyl, then B is preferably substituted by 1 to 3 substituents R4, more preferably 1 or 2 substituents R4. The preferable point or points of attachment of these substituents is para to the point of attachment of B to the four-membered ring when B is substituted by 1 substituent R4 or para and ortho to the point of attachment of B to the four-membered ring when B is substituted by 2 or 3 substituents R4.

In one group of compounds, B represents pyridyl. In this group of compounds, B is preferably substituted by 1 to 3 substituents R4, more preferably 1 or 2 substituents R4. The preferable point or points of attachment of these substituents is para to the point of attachment of B to the four-membered ring when B is substituted by 1 substituent R4 or para and ortho to the point of attachment of B to the four-membered ring when B is substituted by 2 or 3 substituents R4.

In another group of compounds, B is a mono- or bicyclic 5 to 10 membered heteroaromatic ring system containing 1 to 5 heteroatoms, each independently selected from oxygen, nitrogen and sulphur, optionally substituted by one or more R4, provided that B is not pyridyl.

Preferably in this group of compounds, B represents pyrazinyl, pyridazinyl, pyrimidinyl, thienyl, pyrazolyl, thiazolyl, benzothiazolyl, benzoimidazolyl or imidazopyridinyl, each optionally substituted by one or more R4.

More preferably in this group of compounds, B represents pyrazinyl, pyridazinyl, pyrimidinyl, thienyl, pyrazolyl, thiazolyl, benzothiazolyl, benzoimidazolyl, imidazo[4,5 b]pyridinyl or imidazo[4,5 c]pyridinyl, each optionally substituted by one or more R4.

Even more preferably in this group of compounds, B represents pyrazinyl, pyrimidinyl, thienyl, pyrazolyl, thiazolyl, 2-benzothiazolyl, 2-benzoimidazolyl, 2-imidazo[4,5 b]pyridinyl or 2-imidazo[4,5 c]pyridinyl, each optionally substituted by one or more R4.

Yet more preferably in this group of compounds, B represents thienyl or pyrazolyl, each optionally substituted by one or more R4.

In this group of compounds, when B is pyrazinyl, pyridazinyl or pyrimidinyl, then B is preferably substituted by 1 to 3 substituents R4, more preferably 1 or 2 substituents R4. The preferable point or points of attachment of these substituents is para to the point of attachment of B to the four-membered ring when B is substituted by 1 substituent R4 or para and ortho to the point of attachment of B to the four-membered ring when B is substituted by 2 or 3 substituents R4.

In another group of compounds, B represents a 6-membered heterocycle, provided that B is not pyridyl.

In this group of compounds, B is preferably pyrazinyl, pyridazinyl or pyrimidinyl, each optionally substituted by one or more R4.

In this group of compounds, B is more preferably pyrazinyl or pyrimidinyl, each optionally substituted by one or more R4.

In this group of compounds, B is preferably substituted by 1 to 3 substituents R4, more preferably 1 or 2 substituents R4. The preferable point or points of attachment of these substituents is para to the point of attachment of B to the four-membered ring when B is substituted by 1 substituent R4 or para and ortho to the point of attachment of B to the four-membered ring when B is substituted by 2 or 3 substituents R4.

In another group of compounds, B represents a 5-membered heterocycle.

Preferably in this group of compounds, B represents thienyl, pyrazolyl or thiazolyl, each optionally substituted by one or more R4.

More preferably in this group of compounds, B represents thienyl or pyrazolyl, each optionally substituted by one or more R4.

In another group of compounds, B represents an 8- to 10-membered heteroaromatic ring system containing 1 to 5 heteroatoms.

Preferably in this group of compounds, B represents benzothiazolyl, benzoimidazolyl or imidazopyridinyl, each optionally substituted by one or more R4.

Preferably in this group of compounds, B represents benzothiazolyl, benzoimidazolyl, imidazo[4,5 b]pyridinyl or imidazo[4,5 c]pyridinyl, each optionally substituted by one or more R4.

R1 represents hydrogen, hydroxy, C1-C4-alkyl, C1-C4-alkoxy, C1-C4-alkylcarbonyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl.

Preferably, R1 represents hydrogen, C1-C4-alkyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl.

More preferably, R1 is hydrogen

Each R2 independently of one another represents halogen, cyano, C1-C4-alkyl, C1-C4-haloalkyl, C1-C4-alkoxy, C1-C4-haloalkoxy or C1-C4-haloalkylthio.

Preferably, each R2 independently of one another represents halogen, methyl, difluoromethyl or trifluoromethyl.

More preferably, each R2 independently of one another represents halogen, difluoromethyl or trifluoromethyl Yet more preferably, each R2 independently of one another represents halogen or trifluoromethyl.

Even more preferably, each R2 independently of one another represents trifluoromethyl.

In another group of compounds, each R2 is most preferably halogen.

Each R3 independently of one another represents halogen, cyano, C1-C4-alkyl, C3-C4 cycloalkyl, C1-C4-haloalkyl, C1-C4-alkoxy, C1-C4-haloalkoxy or C1-C4-haloalkylthio.

Preferably, each R3 independently of one another represents halogen, C1-C4-alkyl or C1-C4-haloalkyl.

More preferably, each R3 independently of one another represents halogen, C1-C2-alkyl or C1-C2-haloalkyl.

Even more preferably, each R3 independently of one another represents chloro, bromo, methyl or trifluoromethyl.

Most preferably, each R3 independently of one another represents chloro or trifluoromethyl.

Each R4 independently of one another represents halogen, cyano, C1-C4-alkyl, C1-C4-haloalkyl, C1-C4-alkoxy, C1-C4-haloalkoxy, C2-C6-haloalkenyl, C2-C6 haloalkynyl or C3-C6-cycloalkyl optionally substituted by one or more substituents R5 Preferably, each R4 independently of one another represents halogen, cyano, C1-C4-haloalkyl, C1-C4-haloalkoxy, C2-C6-haloalkenyl or C3-C6-cycloalkyl optionally substituted by one or more substituents R5.

More preferably, each R4 independently of one another represents halogen, cyano, C1-C4-haloalkyl, C1-C4-haloalkoxy or C3-C6-cycloalkyl optionally substituted by one or more substituents R5.

Even more preferably, each R4 independently of one another represents halogen or trifluoromethyl.

Most preferably, each R4 independently of one another represents halogen.

Each R5 independently of one another represents halogen, cyano, C1-C4-alkyl, C1-C4-haloalkyl or C1-C4-alkoxycarbonyl.

Preferably, each R5 independently of one another represents halogen, C1-C4-alkyl or C1-C4-haloalkyl.

More preferably, each R5 independently of one another represents halogen or trifluoromethyl.

In one group of compounds, R1 is hydrogen. In this group of compounds, A, B, Y, R1, R2, R3, R4 and R5 are as described herein for a compound of formula (I).

In another group of compounds,

Y represents O or CH2;

A represents phenyl, pyridyl, pyrimidyl, pyrazinyl, pyrazolyl, thienyl or furyl, wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur, optionally substituted by one or more R4;

R1 represents hydrogen;

each R2 independently of one another represents halogen, cyano, C1-C4-alkyl, C1-C4-haloalkyl, C1-C4-alkoxy, C1-C4-haloalkoxy or C1-C4-haloalkylthio;

each R3 independently of one another represents halogen, C1-C4-alkyl or C1-C4-haloalkyl;

each R4 independently of one another represents halogen, cyano, C1-C4-haloalkyl, C1-C4-haloalkoxy, C2-C6-haloalkenyl or C3-C6-cycloalkyl optionally substituted by one or more substituents R5;

each R5 independently of one another represents halogen, C1-C4-alkyl or C1-C4-haloalkyl.

Preferably in this group of compounds, A represents phenyl, 2,-pyridyl, 3-pyridyl, 2-pyrimidyl, 2-pyrazinyl, 2-thienyl, 3-thienyl, 2-furyl or 3-furyl, wherein the phenyl is optionally substituted by one or more R2 and the heteroaromatic ring is optionally substituted by one or more R3.

In another group of compounds,

Y represents O or CH2;

A represents phenyl, pyridyl, pyrimidyl, pyrazinyl, pyrazolyl, thienyl, thiazolyl, or furyl, wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur, optionally substituted by one or more R4;

R1 represents hydrogen;

each R2 independently of one another represent halogen, cyano, C1-C4-alkyl, C1-C4-haloalkyl, C1-C4-alkoxy, C1-C4-haloalkoxy or C1-C4-haloalkylthio;

each R3 independently of one another represent halogen, C1-C4-alkyl or C1-C4-haloalkyl;

each R4 independently of one another represent halogen, cyano, C1-C4-haloalkyl, C1-C4-haloalkoxy or C3-C6-cycloalkyl optionally substituted by one or more substituents R5;

each R5 independently of one another represent selected from halogen, C1-C4-alkyl or C1-C4-haloalkyl.

Preferably in this group of compounds, A represents phenyl, 2,-pyridyl, 3-pyridyl, 2-pyrimidyl, 2-pyrazinyl, 2-thienyl, 3-thienyl, 2-furyl or 3-furyl, wherein the phenyl is optionally substituted by one or more R2 and the heteroaromatic ring is optionally substituted by one or more R3.

In another group of compounds, Y represents O or CH2;

A represents phenyl, pyridyl, pyrimidyl, pyrazinyl, pyrazolyl, thienyl or furyl, wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur optionally substituted by one or more R4;

R1 represents hydrogen;

each R2 independently of one another represents halogen, cyano, C1-C4-alkyl, C1-C4-haloalkyl, C1-C4-alkoxy, C1-C4-haloalkoxy or C1-C4-haloalkylthio;

each R3 independently of one another represents halogen, C1-C4-alkyl or C1-C4-haloalkyl;

each R4 independently of one another represents halogen, cyano, C1-C4-haloalkyl, C1-C4-haloalkoxy or C3-C6-cycloalkyl optionally substituted by one or more substituents R5;

each R5 independently of one another represents halogen, C1-C4-alkyl or C1-C4-haloalkyl.

Preferably in this group of compounds, A represents phenyl, 2-pyridyl, 3-pyridyl, 2-pyrimidyl, 4-pyrimidyl, 2-pyrazinyl, 2-thienyl, 3-thienyl, 4-pyrazolyl, 2-furyl or 3-furyl, wherein the phenyl is optionally substituted by one to three R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one to three R4.

More preferably in this group of compounds, B represents 2-pyridyl, 3-pyridyl, 2-thienyl, 3-thienyl or 4-pyrazolyl, each optionally substituted by one or more R4.

In another group of compounds, Y represents CH2;

A represents phenyl, pyridyl, pyrazinyl or pyrazolyl wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur optionally substituted by one or more R4;

R1 represents hydrogen;

each R2 independently of one another represents halogen, difluoromethyl or trifluoromethyl;

each R3 independently of one another represents halogen, C1-C4-alkyl or C1-C4-haloalkyl;

each R4 independently of one another represents halogen or trifluoromethyl.

Preferably in this group of compounds, A represents phenyl, 2-pyridyl, 3-pyridyl, 2-pyrazinyl or 4-pyrazolyl, wherein the phenyl is optionally substituted by one or two R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4.

More preferably in this group of compounds, B represents 2-pyridyl, 3-pyridyl, 2-thienyl, 3-thienyl or 4-pyrazolyl, each optionally substituted by one or more R4.

Preferably in this group of compounds, each R2 independently of one another represents halogen or trifluoromethyl.

In another group of compounds

Y represents CH2;

A represents phenyl, 2-pyridyl, 3-pyridyl, 2-pyrazinyl or 4-pyrazolyl wherein the phenyl is optionally substituted by one or more R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4;

R1 represents hydrogen;

each R2 independently of one another represents halogen, difluoromethyl or trifluoromethyl;

each R3 independently of one another represents halogen, C1-C2-alkyl or C1-C2-haloalkyl;

each R4 independently of one another represents halogen or trifluoromethyl.

Preferably in this group of compounds, each R2 independently of one another represents halogen or trifluoromethyl.

More preferably in this group of compounds, Y represents CH2;

A represents phenyl, 2-pyridyl, 3-pyridyl, 2-pyrazinyl or 4-pyrazolyl wherein the phenyl is optionally substituted by one R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4;

R1 represents hydrogen;

each R2 independently of one another represents halogen or trifluoromethyl;

each R3 independently of one another represents halogen, methyl or trifluoromethyl;

each R4 independently of one another represents halogen or trifluoromethyl.

More preferably in this group of compounds, B represents 2-pyridyl, 3-pyridyl, 2-thienyl, 3-thienyl or 4-pyrazolyl, each optionally substituted by one or more R4.

In another group of compounds, Y represents CH2;

A represents phenyl, pyridyl, pyrazinyl or pyrazolyl wherein the phenyl is optionally substituted by one or more R2 and the heteroaromatic ring is optionally substituted by one or more R3;

B represents a mono- or bicyclic 5 to 10 membered heteroaromatic ring system containing 1 to 5 heteroatoms, each independently selected from oxygen, nitrogen and sulphur optionally substituted by one or more R4;

R1 represents hydrogen;

each R2 represents trifluoromethyl;

each R3 independently of one another represents halogen, C1-C4-alkyl or C1-C4-haloalkyl; each R4 independently of one another represents halogen.

Preferably in this group of compounds, A represents phenyl, 2-pyridyl, 3-pyridyl, 2-pyrazinyl or 4-pyrazolyl, wherein the phenyl is optionally substituted by one or two R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4.

In another group of compounds
Y represents CH2;

A represents phenyl, 2-pyridyl, 3-pyridyl, 2-pyrazinyl or 4-pyrazolyl wherein the phenyl is optionally substituted by one or more R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4;

R1 represents hydrogen;
each R2 represents trifluoromethyl;
each R3 independently of one another represents halogen, C1-C2-alkyl or C1-C2-haloalkyl;
each R4 independently of one another represents halogen.
Preferably in this group of compounds,
Y represents CH2;

A represents phenyl, 2-pyridyl, 3-pyridyl, 2-pyrazinyl or 4-pyrazolyl wherein the phenyl is optionally substituted by one R2 and the heteroaromatic ring is optionally substituted by one to three R3;

B represents a mono- or bicyclic 5 to 10 membered heteroaromatic ring system containing 1 to 5 heteroatoms, each independently selected from oxygen, nitrogen and sulphur optionally substituted by one or two R4;

R1 represents hydrogen;

each R2 represents trifluoromethyl;

each R3 independently of one another represents halogen, methyl or trifluoromethyl;

each R4 independently of one another represents halogen.

More preferably in this group of compounds, B represents 2-pyridyl, 3-pyridyl, 2-thienyl, 3-thienyl or 4-pyrazolyl, each optionally substituted by one or more R4.

Certain intermediates that can be used to prepare compounds of formula (I) are novel and as such also form part of the invention.

In a further aspect, the invention provides the racemic compounds of formula (II)

wherein Y, B and R1 are as defined herein for a compound of formula (I) provided that B and NHR1 are cis to each other on the four-membered ring.

The preferred definitions of Y, B and R1 defined in respect of compounds of formula (I) also apply to compounds of formula (II).

More preferred definitions of Y and B are those found in table P.

In a further aspect, the invention provides a compound of formula (XIII)

Wherein B is as defined as herein for a compound of formula (I), Prot is a protecting group and Prot' is hydrogen or a protecting group. Preferably Prot' represents H.

The preferred definitions of B defined in respect of compounds of formula (I) also apply to compounds of formula (XIII).

More preferred definitions of B are those found in table P.

Examples of suitable protecting group for compounds of formula (XIII) are carbamates, amides, cyclic imides, sulfonamides, silyl groups and benzyl groups.

Accordingly, in the compounds of formula (XIII), Prot and Prot' each independently of each other represents, for example, carbamates of formula:

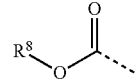

wherein R8 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl, 4-bromobenzyl;

or amides of formula:

wherein R9 represents hydrogen, C1-C4 alkyl, C1-C4 haloalkyl, C1-C4 alkoxyalkyl, C2-C4 alkenyl, benzyl, phenyl optionally substituted by one or more R10; wherein each R10 independently of one another represents halogen, cyano, C1-C4-alkyl, C1-C4-haloalkyl, C1-C4-alkoxy, C1-C4-haloalkoxy C1-C4-haloalkylthio, or nitro;

or cyclic imides of formula:

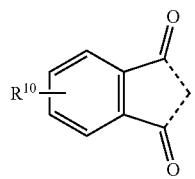

wherein the phenyl ring is optionally substituted by one or more R10 as defined previously;

or sulfonamides of formula:

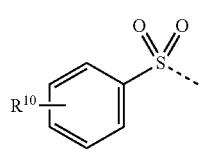

wherein the phenyl ring is optionally substituted by one or more R10 as defined previously;

or silyl groups of formula:

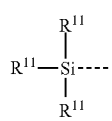

wherein each R11 independently represents C1-C4 alkyl, C1-C4 haloalkyl, C2-C4 alkenyl, benzyl, phenyl optionally substituted by one or more R10 as described previously;

or benzyl groups of formula:

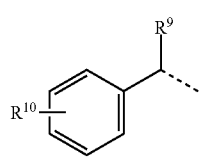

wherein the phenyl ring is optionally substituted by one or more R10 as defined previously; wherein the benzylic position is substituted by R9 as described previously;

Preferably for compounds of formula (XIII), Prot represents carbamates of formula:

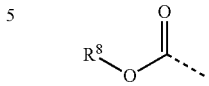

wherein R8 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl, 4-bromobenzyl;

or amides of formula:

wherein R9 represents hydrogen, C1-C4 alkyl, C1-C4 haloalkyl, C1-C4 alkoxylalkyl, C2-C4 alkenyl, benzyl, phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro.

In a further aspect, the invention provides a compound of formula (VI)

(VI)

wherein Y and B are as defined herein for a compound of formula (I).

The preferred definitions of Y and B defined in respect of compounds of formula (I) also apply to compounds of formula (VI).

More preferred definitions of Y and B are those found in table P. A preferred embodiment of the compound of formula (VI) is the compound of formula (XIX), which is a compound of formula (VI) wherein Y is CH2.

In a further aspect, the invention provides a compound of formula (IX)

(IX)

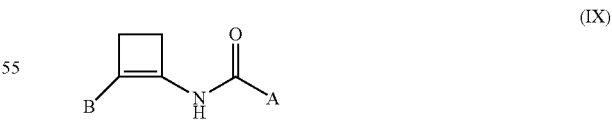

Wherein A and B are as defined herein for a compound of formula (I). The preferred definitions of A and B defined in respect of compounds of formula (I) also apply to compounds of formula (IX).

The preferred definitions of A and B are those found in the relevant entries of tables 1-112.

In a further aspect, the invention provides a compound of formula (XIV)

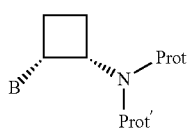
(XIV)

wherein B is as defined herein for a compound of formula (I), and Prot and Prot' are as defined herein for the compounds of formula (XIII). The preferred definitions of B defined in respect of compounds of formula (I) also apply to compounds of formula (XIV). The preferred definitions of Prot and Prot' defined in respect of compounds of formula (XIII) also apply to compounds of formula (XIV). More preferred definitions of B are those found in table P.

In a further aspect, the invention provides a compound of formula (XVI)

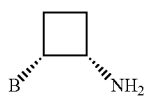
(XVI)

wherein B is as defined herein for a compound of formula (I). The preferred definitions of B defined in respect of compounds of formula (I) also apply to compounds of formula (XVI). More preferred definitions of B are those found in table P.

In a further aspect, the invention provides a compound of formula (X)

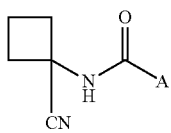
(X)

wherein A is as defined herein for a compound of formula (I). The preferred definitions of A defined in respect of compounds of formula (I) also apply to compounds of formula (X).

More preferred definitions of A are those found in tables 1-56.

In a further aspect, the invention provides a compound of formula (XI)

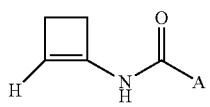
(XI)

wherein A is as defined herein for a compound of formula (I). The preferred definitions of A defined in respect of compounds of formula (I) also apply to compounds of formula (XI).

More preferred definitions of A are those found in tables 1-56.

In a further aspect, the invention provides a compound of formula (XII)

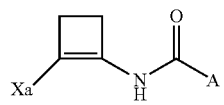
(XII)

wherein A is as defined herein for a compound of formula (I) and Xa is halogen. The preferred definitions of A defined in respect of compounds of formula (I) also apply to compounds of formula (XII). More preferred definitions of A are those found in tables 1-56. Xa is preferably bromide or iodide.

In a further aspect, the invention provides a compound of formula (XX)

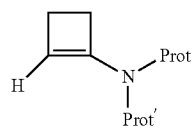
(XX)

wherein Prot and Prot' are as defined herein for a compound of formula (XIII). The preferred definitions of Prot and Prot' defined in respect of compounds of formula (XIII) also apply to compounds of formula (XX).

In a further aspect, the invention provides a compound of formula (XXI)

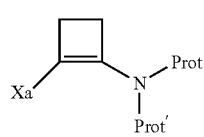
(XXI)

wherein Prot and Prot' are as defined herein for a compound of formula (XIII) and Xa is halogen. The preferred definitions of Prot and Prot' defined in respect of compounds of formula (XIII) also apply to compounds of formula (XXI). The preferred definitions of Xa defined in respect of compound (XII) also apply to compounds of formula (XXI).

In a further aspect, the invention provides a compound of formula (XXIII)

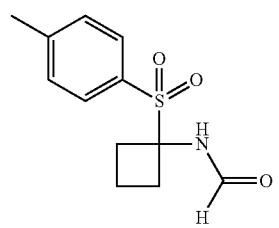
(XXIII)

In a further aspect, the invention provides a compound of formula (XXIV)

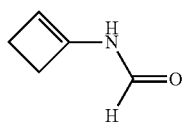

(XXIV)

In a further aspect, the invention provides a compound of formula (XXV)

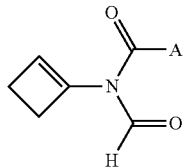

(XXV)

wherein A is as defined herein for a compound of formula (I). The preferred definitions of A defined in respect of compounds of formula (I) also apply to compounds of formula (II).

More preferred definitions of A and B are those found in tables 1-112.

Certain compounds of formula B-M are novel. Accordingly, in a further aspect, the invention provides a compound of formula (XXVII)

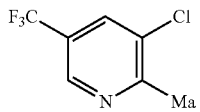

wherein Ma represents a metal, a metal halide, a C1-C4 alkylmetal, a tri(C1-C4alkyl)metal, a tri(C1-C4alkyl)silane, a boronic ester, or a lithium borate. Preferably, Ma is represents a magnesium halide, a zinc halide, C1-C4 alkylzinc, tri(C1-C4alkyl)stannane, tri(C1-C4alkyl)silane, pinacol boronate, N-methyliminodiacetic acid (MIDA) boronic ester or a lithium tri(C1-C4 alkyl)borate.

SCHEME 1

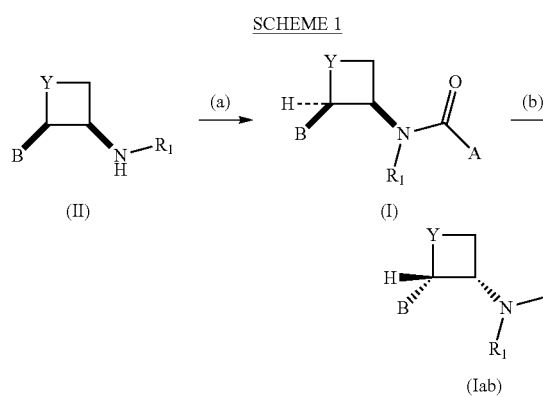

Scheme 1 provides methods of providing the compounds of formula (I) and formula (Iab). Each of these methods form part of the invention.

Step (a)

Compounds of formula (I) may be prepared by reacting a compound of formula (II) with an acylating agent of formula (IV)

A-C(=O)—R*     (IV), in which A is as defined under formula I, and R* is halogen, hydroxyl or $C_{1-6}$ alkoxy, preferably chloro, in the presence of a base, such as triethylamine, Hunig base, sodium bicarbonate, sodium carbonate, potassium carbonate, pyridine or quinoline, but preferably triethylamine, and generally in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxyl, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

Step (b)

Compounds of formula (Iab) or (Iaa), preferably compounds of formula (Iab) may be prepared by resolution of a compound of formula (I), by known methods, for example by recrystallization from an optically active solvent, by chromatography on chiral adsorbents, for example high-performance liquid chromatography (HPLC) on acetyl cellulose, with the aid of suitable microorganisms, by cleavage with specific, enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

SCHEME 2

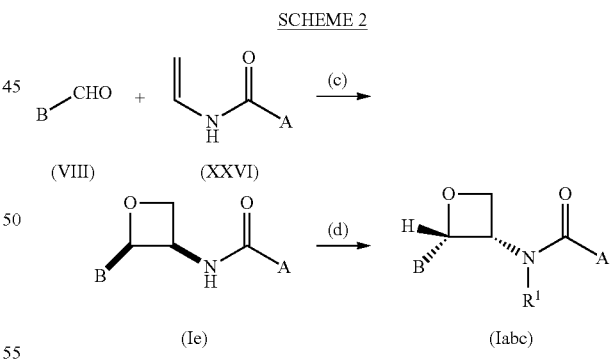

Scheme 2 provides methods of providing the compounds of formula (Ie), that is a compound of formula (I) wherein Y is O and R1 is H, and compounds of formula (Iabc), that is a compound of formula (Iab) wherein Y is O and R1 is H. Each of these methods form part of the invention.

Step (c) Compounds of the formula (Ie) can be made by 2+2 cycloaddition of aldehydes of the formula (VIII) wherein B is defined under formula (I) and enamides of the formula (XXVI) wherein A is as defined under formula (I). This can be performed with the assistance of UV radiation as described by Bach et al. (Journal of Organic Chemistry (1999), 64(4), 1265-1273). The compounds of formula (Ie) may be accompanied by their trans isomers.

Step (d)

Compounds of formula (Iabc), that is a compound of formula (Iab) wherein Y is O and R1 is H, may be prepared by resolution of a compound of formula (Ie), by known methods, for example by recrystallization from an optically active solvent, by chromatography on chiral adsorbents, for example high-performance liquid chromatography (HPLC) on acetyl cellulose, with the aid of suitable microorganisms, by cleavage with specific, enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

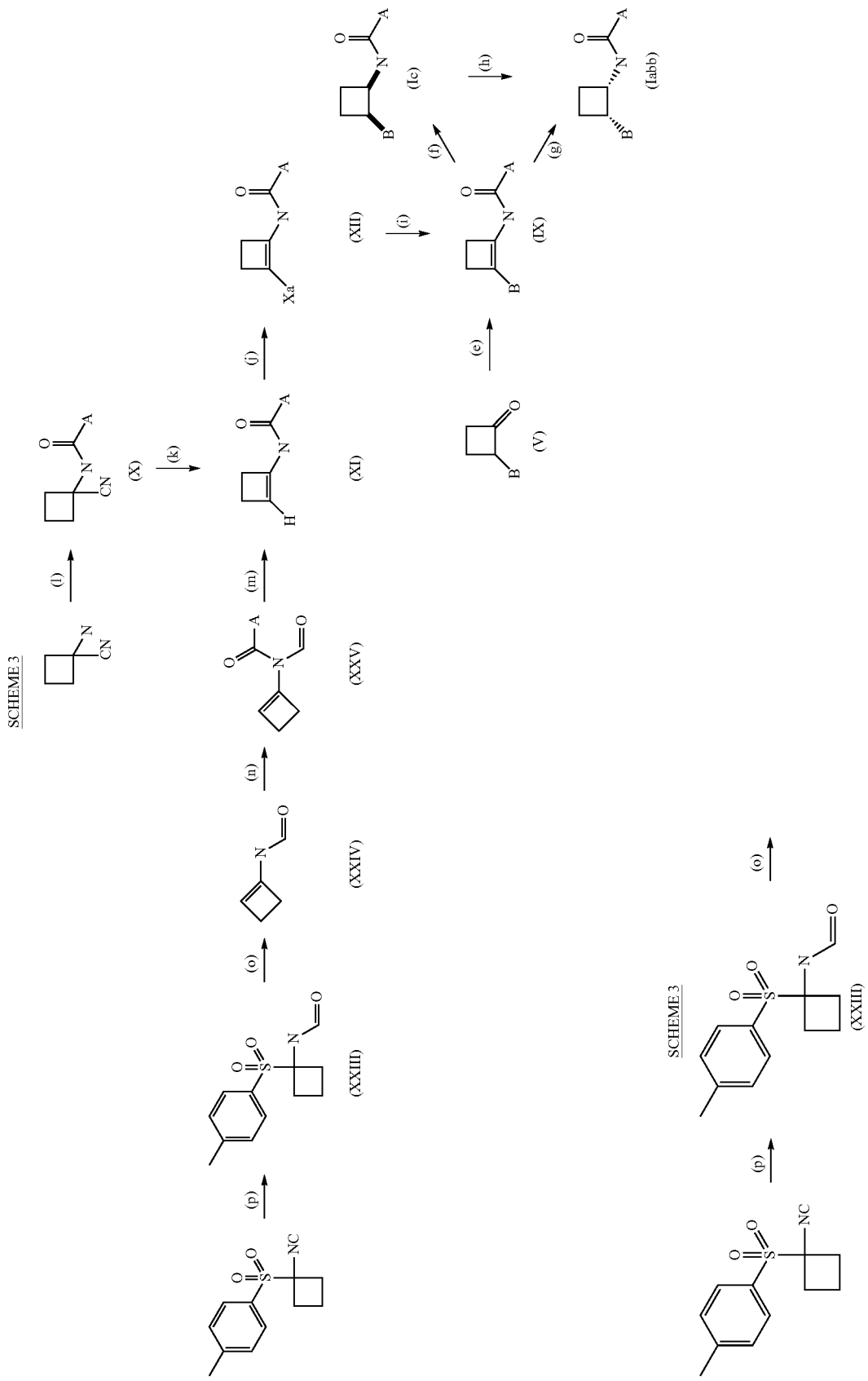

-continued
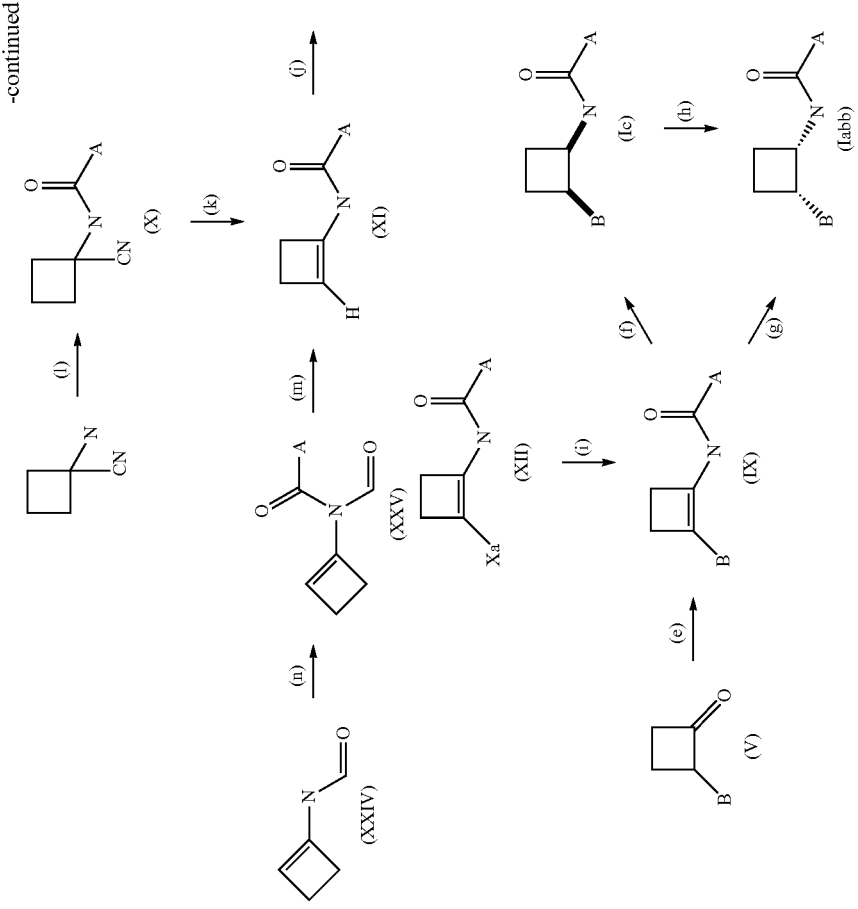

Scheme 3 provides methods of providing the compounds of formula (Ic), that is a compound of formula (I) wherein Y is CH2 and R1 is H, compounds of formula (Iabb), that is a compound of formula (Iab) wherein Y is CH2 and R1 is H, compounds of formula (IX), compounds of formula (XII), compounds of the formula (XI), compounds of the formula (X), compounds of formula (XXV), compounds of formula (XXIV) and compounds of formula (XXIII). Each of these methods form part of the invention.

Step (e)

Compounds of the formula (IX) can be prepared from ketones of the formula (V) by treatment with titanium tetraalkoxide and ammonia followed by treatment with an acid chloride of the formula A-CO—Cl, wherein A is as defined herein for a compound of formula (I).

Step (f)

The compound of formula (Ic) can be prepared by reduction of the compound of formula (IX). Use of a racemic or achiral catalyst gives a compound of formula (Ic).

Step (q)

The compound of formula (Iabb) can be prepared by reduction of the compound of formula (IX). A chiral or enantioenriched catalyst can be used to prepare the compounds of formula (Iabb).

Step (h)

Compounds of formula (Iabb) may be prepared by resolution of a compound of formula (Ic) by known methods, for example by recrystallization from an optically active solvent, by chromatography on chiral adsorbents, for example high-performance liquid chromatography (HPLC) on acetyl cellulose, with the aid of suitable microorganisms, by cleavage with specific, enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Step (i)

Compounds of the formula (IX) can also be formed by treatment of compounds of the formula (XII), wherein Xa is a halogen, preferably chlorine, bromine or iodine, and A is as defined herein for compounds of formula (I), with an heteroarylating agent of the formula B-M, wherein B is as defined herein for compounds of formula (I) and M is a metal or metalloid. Examples of B-M are heteroaryl lithium, heteroaryl Grignard, heteroaryl zinc halide, heteroaryl boronic acid or boronate or heteroaryl trimethylsilane or heteroaryl stannanes or heteroaryl lithium boratonates. The preparation of the heteroaryl boronic esters such as pinacol boronates or N-methyliminodiacetic acid (MIDA) boronic esters and Heteroaryl lithium boratonates are described by Burke et al. in Angewandte Chemie 2012, 51, p 2667-2672.

The coupling of B-M with (XII) is assisted by catalysis. Typical catalysts are transition metal catalysts. Typical transition metal catalysts are salts of palladium, nickel, cobalt, or iron. These salts are often complexed with ligands such as phosphines, amines or carbenes.

Step (j)

Compounds of formula (XII) can be prepared by treatment of compounds of the formula (XI), wherein A is as defined herein for the compounds of formula (I), with a halogenating agent. Common halogenating agents are N-bromosuccinimide, N-chlorosuccinimide, N-iodosuccinimide, Cl2, Br2 and I2.

Step (k)

Compounds of formula (XI) can be prepared by treatment of compounds of the formula (X), wherein A is as defined herein for the compounds of formula (I), with a base. Typical bases that can be used for this transformation are metal alkoxides, metal hydrides, and metal amides. Preferred bases are metal alkoxides, in particular sodium alkoxide, most particularly sodium t-butoxide.

Step (l)

Compounds of formula (X) can be prepared by acylation of 1-cyano-cyclobutanamine with an acylating agent of the formula (IV), using methodology described above for the synthesis of compounds of formula (I) from compounds of formula (II).

Step (m)

Compounds of formula (XI) can also be prepared by selective hydrolysis of compounds of formula (XXV) by using a base. Typical bases that can be used for this transformation are metal alkoxides, metal carbonates. Alternatively compounds of formula (XXV) can be heated in alcohols such as ethanol or isopropanol.

Step (n)

Compounds of formula (XXV) can be prepared by acylation of compounds of formula (XXIV) with an acylating agent of the formula (IV), using methodology described above under step (a).

Step (o)

Compound of formula (XXIV) can be prepared by treatment of compounds of formula (XXIII) using a base. Typical bases that can be used for this transformation are metal alkoxides, metal hydrides, and metal amides. Preferred bases are metal alkoxides, in particular sodium alkoxide, most particularly sodium t-butoxide.

Step (p)

Compound of formula (XXIII) can be prepared by hydrolysis of known compound 1-(1-isocyanocyclobutyl)sulfonyl-4-methyl-benzene by the use of acid. Typical acids that can be used for this transformation are mineral acids such as hydrochloric acid, sulphuric acid, or carboxylic acids such as acetic acid or citric acid.

SCHEME 4

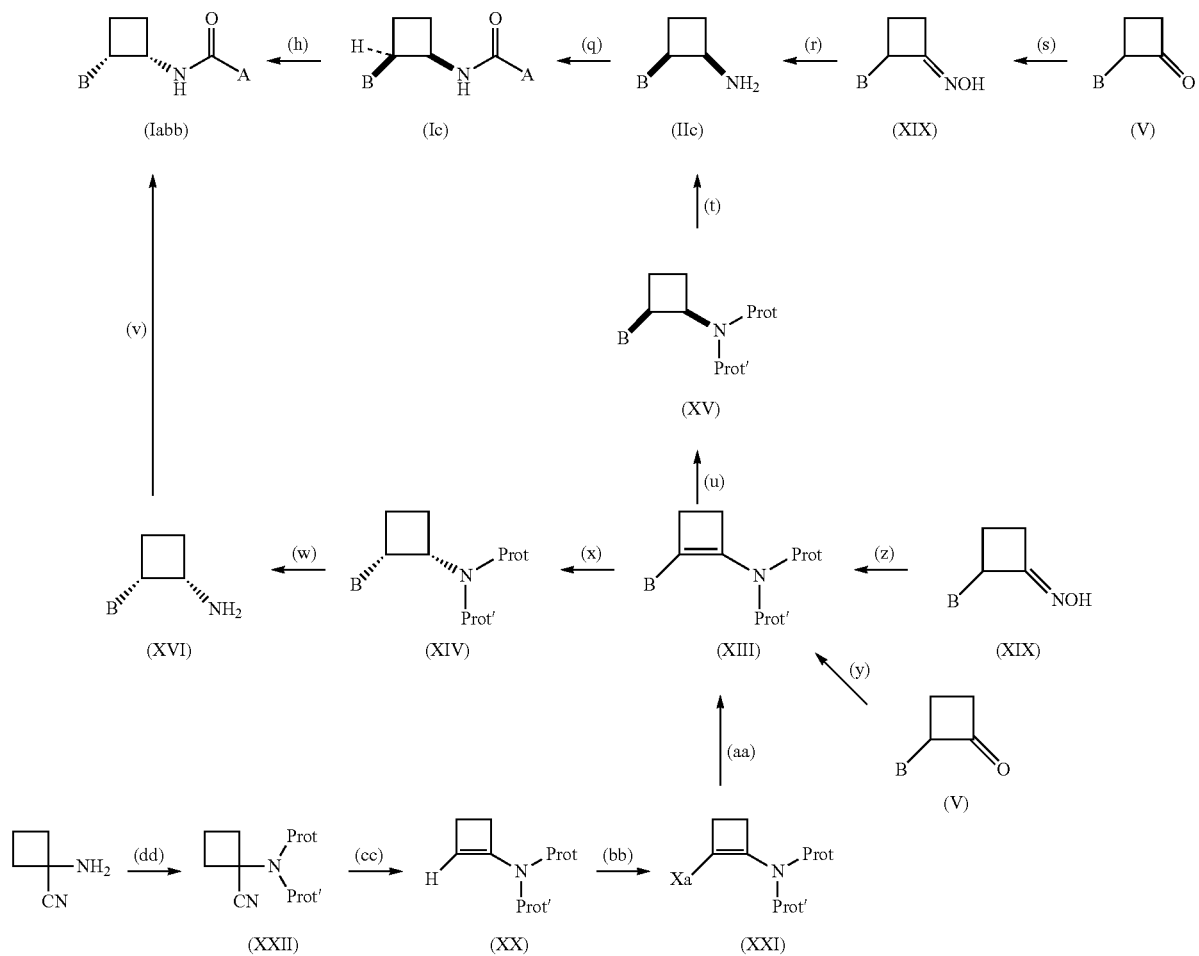

Scheme 4 provides methods of providing the compounds of formula (Ic), compounds of formula (Iabb), compounds of formula (IIc) that is a compound of formula (II) wherein Y is CH2 and R1 is H, compounds of formula (XIX), that is a compound of formula (VI) wherein Y is CH2, compounds of the formula (XV) wherein Prot and Prot' are as defined herein for a compound of formula (XIII), compounds of the formula (XIV), compounds of the formula (XVI), compounds of formula (XIII), compounds of formula (XXI), compounds of formula (XX) and compounds of formula (XXII) wherein Prot and Prot' are as defined herein for a compound of formula (XIII). Each of these methods form part of the invention.

Step (q)

Compounds of the formula (Ic) can be also be formed by treatment of amines of the formula (IIc) with an acylating agent of the formula (IV) using methodology described above under step (a).

Step (r)

Compounds of the formula (IIc) can be prepared by reduction of the compound of formula (XIX) wherein B is defined under formula (I). D. E. Nichols et al. (J. Med. Chem 1984, 27, 1108-11) describe methods for this reduction. Certain methods may yield trans isomers as side-products.

Step (s)

Compounds of the formula (XIX) can be prepared from the compound of formula (V) by the action of hydroxylamine, or by the combination of a hydroxylamine salt and a base.

Step (t)

Amines of the formula (IIc) can also be formed by deprotection of compounds of the formula (XV). Protected amine groups are well known for example in P. G. M. Wuts and T. W. Greene in Greene's Protective Groups in Organic Synthesis 4$^{th}$ Edn. Wiley 2007. pp 696-926. The methods of deprotection depend on the protecting group and are well known and described in Wuts and Greene. Preferred protecting groups are amides and carbamates.

Step (u)

The compounds of formula (XV) are prepared by reduction of the compounds of formula (XIII). This reduction is preferably performed with molecular hydrogen, preferably in the presence of a catalyst. The catalyst is preferably a metal salt or metal complex, where the metal is preferably a transition metal (e.g. Ir, Rh, Pd, Ni and Ru). Achiral or racemic will lead to compounds of the formula (XV).

Step (v)

Compounds of the formula (Iabb) can be also be formed by treatment of amines of the formula (XVI), wherein B is as defined herein for a compound of formula (I), with an acylating agent of the formula (IV) using methodology described above under step (a).

Step (w).

Compounds of the formula (XVI) are formed by deprotection of compounds of the formula (XIV) using the methodology described under step (t).

Step (x)

The compounds of formula (XIV) are prepared by reduction of the compounds of formula (XIII). This reduction is preferably performed with molecular hydrogen, preferably in the presence of a catalyst. The catalyst is preferably a metal salt or metal complex, where the metal is preferably a transition metal (e.g. Ir, Rh, Pd, Ni and Ru). Enantioenriched catalysts lead to compounds of the formula (XIV).

Step (y)

Compounds of the formula (XIII) can be prepared by treatment of the compounds of formula (V) with ammonia and titanium tetraalkoxide followed by treatment with a derivatisation agent. Preferred derivating agents are acid chloride and anhydrides. Examples of this methodology are described in Reeves et al, Angew. Chem. Int. Ed., 2012, 51, 1400-1404.

Step (z)

Compounds of the formula (XIII) can also be formed by treatment of compounds of formula (XIX) with a reducing agent in the presence of an acylating agent. Preferred reducing agents are iron metal, an iron II salt or a phosphine. Preferred acylation agent is acetic anhydride. Examples of this methodology can be found in Guan, Z-H. et al. J. Org. Chem. (2011), 76(1), 339-341, and references cited therein.

Step (aa)

Compounds of the formula (XIII) can also be formed by treatment of compounds of the formula (XXI) with an arylating agent of the formula B-M, where B is as defined in formula I, and M is a metal or metalloid. Examples of B-M are heteroaryl lithium, heteroaryl Grignard, heteroaryl zinc halide, heteroaryl boronic acid or boronate, heteroaryl stannanes or heteroaryl trimethylsilane. The coupling of B-M with (XXI) is assisted by catalysis. Typical catalysts are transition metal catalysts. Typical transition metal catalysts are salts of palladium, nickel, cobalt, or iron. These salts are often complexed with ligands such as phosphines, amines or carbenes.

Step (bb)

Compounds of the formula (XXI) can be prepared by treatment of the compounds of the formula (XX) with a halogenating agent. Common halogenating agents are N-bromosuccinimide, N-chlorosuccinimide, N-iodosuccinimide, Cl2, Br2, and I2.

Step (cc)

Compounds of the formula (XX) can be prepared by treatment of compounds of the formula (XXII) with a base. Typical bases that can be used for this transformation are metal alkoxides, metal hydrides, and metal amides. Preferred bases are metal alkoxides, in particular sodium alkoxide, most particularly sodium t-butoxide.

Step (dd)

Compounds of the formula (XXII) can be prepared by protection of 1-cyano-cyclobutanamine with protecting groups Prot and Prot'. Protected amine groups are well known for example in P. G. M. Wuts and T. W. Greene in Greene's Protective Groups in Organic Synthesis 4$^{th}$ Edn. Wiley 2007. pp 696-926. The methods of protection depend on the protecting group and are well known and described in Wuts and Greene. Preferred protecting groups are amides and carbamates.

For preparing all further compounds of the formula (I) functionalized according to the definitions of A, B, Y, $R_1$, $R_2$, $R_3$, $R_4$, $R_5$ and $R_6$ there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

Diastereomer mixtures or racemate mixtures of compounds of formula (I), in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615 or C. White, Science, vol 318, p. 783, 2007.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

Tables 1 to 112: Compounds of Formula (Ia) and Compounds of Formula (Ib)

The invention is further illustrated by making available the following individual compounds of formula (Ia) listed below in Tables 1 to 56 and the following individual compounds of formula (Ib) listed below in tables 57 to 112

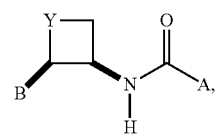

(Ia)

Each of Tables 1 to 56, which follow the Table P below, make available 15 compounds of the formula (Ia) in which Y and B are the substituents defined in Table P and A is the substituent defined in the relevant Table 1 to 56. Thus Table 1 individualises 15 compounds of formula (Ia) wherein for each row of Table P, the A substituent is as defined in Table 1; similarly, Table 2 individualises 15 compounds of formula (Ia) wherein for each row of Table P, the A substituent is as defined in Table 2; and so on for Tables 3 to 56.

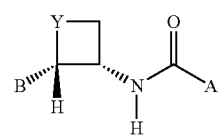

(Ib)

Each of Tables 57 to 112, which follow the Table P below, make available 15 compounds of the formula (Ib) in which Y and B are the substituents defined in Table P and A is the substituent defined in the relevant Table 57 to 112. Thus Table 57 individualises 15 compounds of formula (Ib) wherein for each row of Table P, the A substituent is as defined in Table 57; similarly, Table 58 individualises 15 compounds of formula (Ib) wherein for each row of Table P, the A substituent is as defined in Table 58; and so on for Tables 59 to 112.

TABLE P

| Compound No. | Y | B |
|---|---|---|
| P.001 | $CH_2$ | 3-chloro-5-trifluoromethyl-pyridin-2-yl |
| P.002 | $CH_2$ | 6-chloro-pyridin-3-yl |
| P.003 | $CH_2$ | 6-trifluoromethyl-pyridin-3-yl |
| P.004 | $CH_2$ | 3-methyl-thien-2-yl |
| P.005 | $CH_2$ | 3-chloro-thien-2-yl |
| P.006 | $CH_2$ | 4-chloro-1-methyl-1H-pyrazol-3-yl |
| P.007 | $CH_2$ | 3,5-dichloro-pyridin-2-yl |
| P.008 | $CH_2$ | 2,6-dichloro-pyridin-3-yl |
| P.009 | $CH_2$ | 2-chloro-6-trifluoromethyl-pyridin-3-yl |
| P.010 | $CH_2$ | 4-chloro-6-trifluoromethyl-pyridin-3-yl |
| P.011 | $CH_2$ | 2-fluoro-5-chloro-pyrid-3-yl |
| P.012 | $CH_2$ | 3-fluoro-5-chloro-pyrid-2-yl |
| P.013 | $CH_2$ | 2-chloro-pyrid-4-yl |
| P.014 | O | 5-fluoromethyl-pyridin-2-yl |
| P.015 | $CH_2$ | 3-chloro-2-pyridyl |

Table 1 provides 15 compounds of formula (Ia), wherein A is

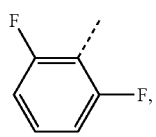

(A1)

(2,6-difluorophenyl) wherein the broken line indicates the point of attachment of the group A to the amide group, and Y and B are as defined in each row of Table P. For example, compound 1.001 has the following structure:

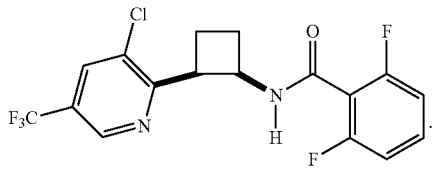
(1.001)

Table 2 provides 15 compounds of formula (Ia) wherein A is 2-chloro-3-pyrazinyl (A2) and Y and B are as defined in each row of Table P.

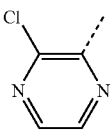

Table 3 provides 15 compounds of formula (Ia) wherein A is 3-trifluoromethyl-2-pyridyl (A3) and Y and B are as defined in each row of Table P.

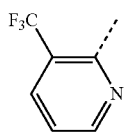

Table 4 provides 15 compounds of formula (Ia) wherein A is 3-chloro-2-pyridyl (A4) and Y and B are as defined in each row of Table P.

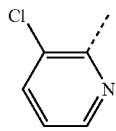

Table 5 provides 15 compounds of formula (Ia) wherein A is 2-trifluoromethyl-3-pyridyl (A5) and Y and B are as defined in each row of Table P.

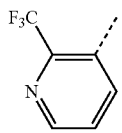

Table 6 provides 15 compounds of formula (Ia) wherein A is 2-trifluoromethyl-phenyl (A6) and Y and B are defined in each row of Table P.

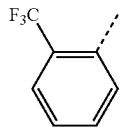

Table 7 provides 15 compounds of formula (Ia) wherein A is 2-chloro-3-pyridyl (A7) and Y and B are as defined in each row of Table P.

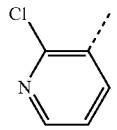

Table 8 provides 15 compounds of formula (Ia) wherein A is 2-fluoro-6-trifluoromethyl-phenyl (A8) and Y and B are as defined in each row of Table P.

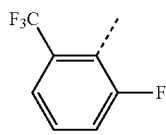

Table 9 provides 15 compounds of formula (Ia) wherein A is 2-tolyl (A9) and Y and B are as defined in each row of Table P.

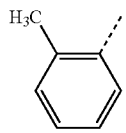

Table 10 provides 15 compounds of formula (Ia) wherein A is 2-pyrimidinyl (A10) and Y and B are as defined in each row of Table P.

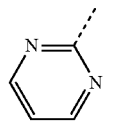

Table 11 provides 15 compounds of formula (Ia) wherein A is 3-methyl-2-pyridyl (A11) and Y and B are as defined in each row of Table P.

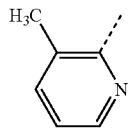

Table 12 provides 15 compounds of formula (Ia) wherein A is 2-fluorophenyl (A12) and Y and B are as defined in each row of Table P.

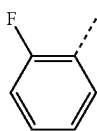

Table 13 provides 15 compounds of formula (Ia) wherein A is 2-chlorophenyl (A13) and Y and B are as defined in each row of Table P.

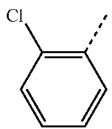

Table 14 provides 15 compounds of formula (Ia) wherein A is 2-bromophenyl (A14) and Y and B are as defined in each row of Table P.

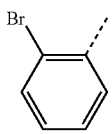

Table 15 provides 15 compounds of formula (Ia) wherein A is 2-iodophenyl (A15) and Y and B are as defined in each row of Table P.

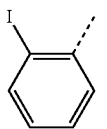

Table 16 provides 15 compounds of formula (Ia) wherein A is 2,6-dichlorophenyl (A16) and Y and B are as defined in each row of Table P.

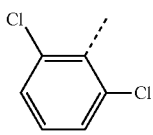

Table 17 provides 15 compounds of formula (Ia) wherein A is 2-chloro-6-fluoro-phenyl (A17) and Y and B are as defined in each row of Table P.

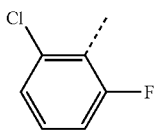

Table 18 provides 15 compounds of formula (Ia) wherein A is 2,4,6-trifluorophenyl (A18) and Y and B are as defined in each row of Table P.

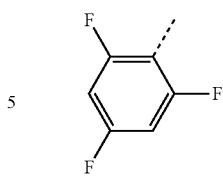

Table 19 provides 15 compounds of formula (Ia) wherein A is 2-trifluoromethoxy-phenyl (A19) and Y and B are as defined in each row of Table P.

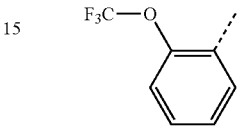

Table 20 provides 15 compounds of formula (Ia) wherein A is 2-fluoro-6-methyl-phenyl (A20) and Y and B are as defined in each row of Table P.

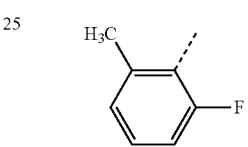

Table 21 provides 15 compounds of formula (Ia) wherein A is 2-fluoro-6-methoxy-phenyl (A21) and Y and B are as defined in each row of Table P.

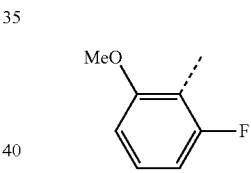

Table 22 provides 15 compounds of formula (Ia) wherein A is 2-methyl-3-pyridyl (A22) and Y and B are as defined in each row of Table P.

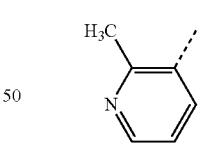

Table 23 provides 15 compounds of formula (Ia) wherein A is 3-fluoro-2-pyridyl (A23) and Y and B are as defined in each row of Table P.

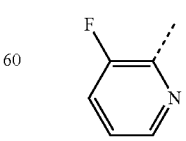

Table 24 provides 15 compounds of formula (Ia) wherein A is 3-methyl-2-pyrazinyl (A24) and Y and B are as defined in each row of Table P.

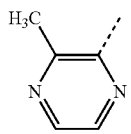

Table 25 provides 15 compounds of formula (Ia) wherein A is 3-bromo-2-pyrazinyl (A25) and Y and B are as defined in each row of Table P.

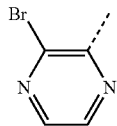

Table 26 provides 15 compounds of formula (Ia) wherein A is 3-trifluoromethyl-2-pyrazinyl (A26) and Y and B are as defined in each row of Table P.

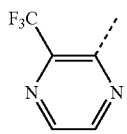

Table 27 provides 15 compounds of formula (Ia) wherein A is 2-methyl-3-furyl (A27) and Y and B are as defined in each row of Table P.

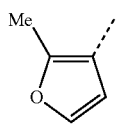

Table 28 provides 15 compounds of formula (Ia) wherein A is 5-chloro-4-pyrimidinyl (A28) and Y and B are as defined in each row of Table P.

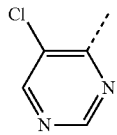

Table 29 provides 15 compounds of formula (Ia) wherein A is 2-cyanophenyl (A29) and Y and B are as defined in each row of Table P.

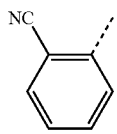

Table 30 provides 15 compounds of formula (Ia) wherein A is 2-trifluoromethylthio-phenyl (A30) and Y and B are as defined in each row of Table P.

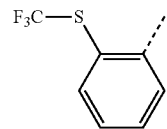

Table 31 provides 15 compounds of formula (Ia) wherein A is 3-bromo-2-pyridyl (A31) and Y and B are as defined in each row of Table P.

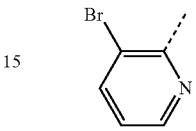

Table 32 provides 15 compounds of formula (Ia) wherein A is 5-bromo-4-thiazolyl (A32) and Y and B are as defined in each row of Table P.

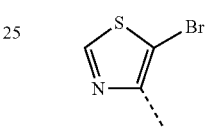

Table 33 provides 15 compounds of formula (Ia) wherein A is 2-trifluoromethyl-3-thienyl (A33) and Y and B are as defined in each row of Table P.

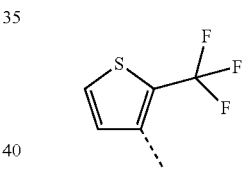

Table 34 provides 15 compounds of formula (Ia) wherein A is 2-iodo-3-thienyl (A34) and Y and B are as defined in each row of Table P.

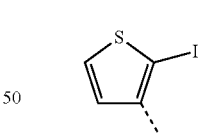

Table 35 provides 15 compounds of formula (Ia) wherein A is 2-chloro-3-thienyl(A35) and Y and B are as defined in each row of Table P.

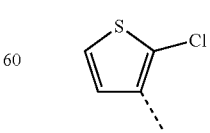

Table 36 provides 15 compounds of formula (Ia) wherein A is 3-bromo-2-thienyl (A36) and Y and B are as defined in each row of Table P.

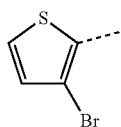

Table 37 provides 15 compounds of formula (Ia) wherein A is 3-chloro-2-thienyl (A37) and Y and B are as defined in each row of Table P.

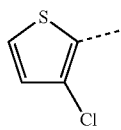

Table 38 provides 15 compounds of formula (Ia) wherein A is 2-bromo-3-thienyl (A38) and Y and B are as defined in each row of Table P.

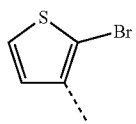

Table 39 provides 15 compounds of formula (Ia) wherein A is 4-methyl-5-[1,2,3]-thiadiazolyl (A39) and Y and B are as defined in each row of Table P.

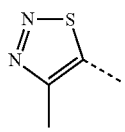

Table 40 provides 15 compounds of formula (Ia) wherein A is 4-cyclopropyl-5-[1,2,3]-thiadiazolyl (A40) and Y and B are as defined in each row of Table P.

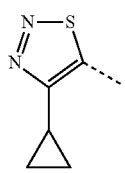

Table 41 provides 15 compounds of formula (Ia) wherein A is 3-methyl-4-isothiazolyl (A41) and Y and B are as defined in each row of Table P.

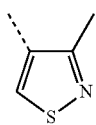

Table 42 provides 15 compounds of formula (Ia) wherein A is 5-methyl-4-isoxazolyl (A42) and Y and B are as defined in each row of Table P.

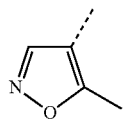

Table 43 provides 15 compounds of formula (Ia) wherein A is 5-cyclopropyl-4-isoxazolyl (A43) and Y and B are as defined in each row of Table P.

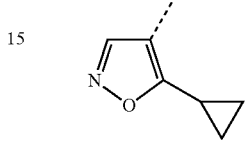

Table 44 provides 15 compounds of formula (Ia) wherein A is 2-(trifluoromethyl)furan-3-yl (A44) and Y, and B are as defined in each row of Table P.

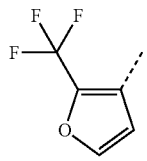

Table 45 provides 14 compounds of formula (Ia) wherein A is 2-bromofuran-3-yl (A45) and Y, and B are as defined in each row of Table P.

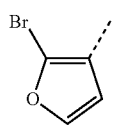

Table 46 provides 15 compounds of formula (Ia) wherein A is 4-(trifluoromethyl)pyridazin-3-yl (A46) and Y, and B are as defined in each row of Table P.

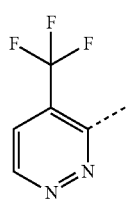

Table 47 provides 15 compounds of formula (Ia) wherein A is 3,6-difluoro-2-(trifluoromethyl) phenyl (A47) and Y, and B are as defined in each row of Table P.

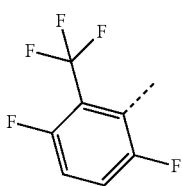

Table 48 provides 15 compounds of formula (Ia) wherein A is 2-bromo-3,6-difluorophenyl (A48) and Y, and B are as defined in each row of Table P.

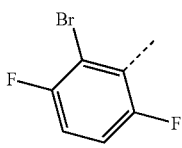

Table 49 provides 15 compounds of formula (Ia) wherein A is 2-chloro-3,6-difluorophenyl (A49) and Y, and B are as defined in each row of Table P.

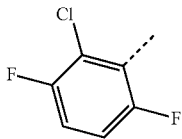

Table 50 provides 15 compounds of formula (Ia) wherein A is 4-(trifluoromethyl)pyrimidin-5-yl (A50) and Y, and B are as defined in each row of Table P.

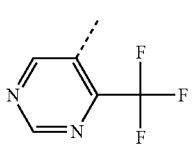

Table 51 provides 15 compounds of formula (Ia) wherein A is 4-(trifluoromethyl)pyrid-3-yl (A51) and Y, and B are as defined in each row of Table P.

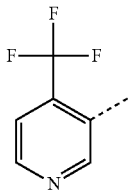

Table 52 provides 15 compounds of formula (Ia) wherein A is 3-(difluoromethyl)-1-methylpyrazol-4-yl (A52) and Y, and B are as defined in each row of Table P.

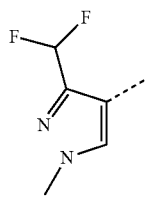

Table 53 provides 15 compounds of formula (Ia) wherein A is 4-methyloxazol-5-yl (A53) and Y, and B are as defined in each row of Table P.

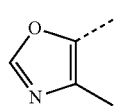

Table 54 provides 15 compounds of formula (Ia) wherein A is 3-methoxypyrid-2-yl (A54) and Y, and B are as defined in each row of Table P.

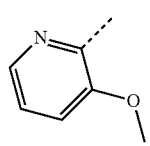

Table 55 provides 15 compounds of formula (Ia) wherein A is 2-chlorofuran-3-yl (A55) and Y, and B are as defined in each row of Table P.

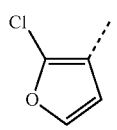

Table 56 provides 15 compounds of formula (Ia) wherein A is 2-iodofuran-3-yl (A56) and Y, and B are as defined in each row of Table P.

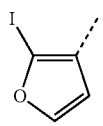

Table 57 provides 15 compounds of formula (Ib), wherein A is 2,6-difluorophenyl (A1 as defined in table 1) and Y and B are as defined in each row of Table P.

Table 58 provides 15 compounds of formula (Ib) wherein A is 2-chloro-3-pyrazinyl (A2 as defined in table 2) and Y and B are as defined in each row of Table P.

Table 59 provides 15 compounds of formula (Ib) wherein A is 3-trifluoromethyl-2-pyridyl (A3 as defined in table 3) and Y and B are as defined in each row of Table P.

Table 60 provides 15 compounds of formula (Ib) wherein A is 3-chloro-2-pyridyl (A4 as defined in table 4) and Y and B are as defined in each row of Table P.

Table 61 provides 15 compounds of formula (Ib) wherein A is 2-trifluoromethyl-3-pyridyl (A5 as defined in table 5) and Y and B are as defined in each row of Table P.

Table 62 provides 15 compounds of formula (Ib) wherein A is 2-trifluoromethyl-phenyl (A6 as defined in table 6) and Y and B are as defined in each row of Table P.

Table 63 provides 15 compounds of formula (Ib) wherein A is 2-chloro-3-pyridyl (A7 as defined in table 7) and Y and B are as defined in each row of Table P.

Table 64 provides 15 compounds of formula (Ib) wherein A is 2-fluoro-6-trifluoromethyl-phenyl (A8 as defined in table 8) and Y and B are as defined in each row of Table P.

Table 65 provides 15 compounds of formula (Ib) wherein A is 2-tolyl (A9 as defined in table 9) and Y and B are as defined in each row of Table P.

Table 66 provides 15 compounds of formula (Ib) wherein A is 2-pyrimidinyl (A10 as defined in table 10) and Y and B are as defined in each row of Table P.

Table 67 provides 15 compounds of formula (Ib) wherein A is 3-methyl-2-pyridyl (A11 as defined in table 11) and Y and B are as defined in each row of Table P.

Table 68 provides 15 compounds of formula (Ib) wherein A is 2-fluorophenyl (A12 as defined in table 12) and Y and B are as defined in each row of Table P.

Table 69 provides 15 compounds of formula (Ib) wherein A is 2-chlorophenyl (A13 as defined in table 13) and Y and B are as defined in each row of Table P.

Table 70 provides 15 compounds of formula (Ib) wherein A is 2-bromophenyl (A14 as defined in table 14) and Y and B are as defined in each row of Table P.

Table 71 provides 15 compounds of formula (Ib) wherein A is 2-iodophenyl (A15 as defined in table 15) and Y and B are as defined in each row of Table P.

Table 72 provides 15 compounds of formula (Ib) wherein A is 2,6-dichlorophenyl (A16 as defined in table 16) and Y and B are as defined in each row of Table P.

Table 73 provides 15 compounds of formula (Ib) wherein A is 2-chloro-6-fluoro-phenyl (A17 as defined in table 17) and Y and B are as defined in each row of Table P.

Table 74 provides 15 compounds of formula (Ib) wherein A is 2,4,6-trifluorphenyl (A18 as defined in table 18) and Y and B are as defined in each row of Table P.

Table 75 provides 15 compounds of formula (Ib) wherein A is 2-trifluoromethoxy-phenyl (A19 as defined in table 19) and Y and B are as defined in each row of Table P.

Table 76 provides 15 compounds of formula (Ib) wherein A is 2-fluoro-6-methyl-phenyl (A20 as defined in table 20) and Y and B are as defined in each row of Table P.

Table 77 provides 15 compounds of formula (Ib) wherein A is 2-fluoro-6-methoxy-phenyl (A21 as defined in table 21) and Y and B are as defined in each row of Table P.

Table 78 provides 15 compounds of formula (Ib) wherein A is 2-methyl-3-pyridyl (A22 as defined in table 22) and Y and B are as defined in each row of Table P.

Table 79 provides 15 compounds of formula (Ib) wherein A is 3-fluoro-2-pyridyl (A23 as defined in table 23) and Y and B are as defined in each row of Table P.

Table 80 provides 15 compounds of formula (Ib) wherein A is 3-methyl-2-pyrazinyl (A24 as defined in table 24) and Y and B are as defined in each row of Table P.

Table 81 provides 15 compounds of formula (Ib) wherein A is 3-bromo-2-pyrazinyl (A25 as defined in table 25) and Y and B are as defined in each row of Table P.

Table 82 provides 15 compounds of formula (Ib) wherein A is 3-trifluoromethyl-2-pyrazinyl (A26 as defined in table 26) and Y and B are as defined in each row of Table P.

Table 83 provides 15 compounds of formula (Ib) wherein A is 2-methyl-3-furyl (A27 as defined in table 27) and Y and B are as defined in each row of Table P.

Table 84 provides 15 compounds of formula (Ib) wherein A is 5-chloro-4-pyrimidinyl (A28 as defined in table 28) and Y and B are as defined in each row of Table P.

Table 85 provides 15 compounds of formula (Ib) wherein A is 2-cyanophenyl (A29 as defined in table 29) and Y and B are as defined in each row of Table P.

Table 86 provides 15 compounds of formula (Ib) wherein A is 2-trifluoromethylthio-phenyl (A30 as defined in table 30) and Y and B are as defined in each row of Table P.

Table 87 provides 15 compounds of formula (Ib) wherein A is 3-bromo-2-pyridyl (A31 as defined in table 31) and Y and B are as defined in each row of Table P.

Table 88 provides 15 compounds of formula (Ib) wherein A is 5-bromo-4-thiazolyl (A32 as defined in table 32) and Y and B are as defined in each row of Table P.

Table 89 provides 15 compounds of formula (Ib) wherein A is 2-trifluoromethyl-3-thienyl (A33 as defined in table 33) and Y and B are as defined in each row of Table P.

Table 90 provides 15 compounds of formula (Ib) wherein A is 2-iodo-3-thienyl (A34 as defined in table 34) and Y and B are as defined in each row of Table P.

Table 91 provides 15 compounds of formula (Ib) wherein A is 2-chloro-3-thienyl (A35 as defined in table 35) and Y and B are as defined in each row of Table P.

Table 92 provides 15 compounds of formula (Ib) wherein A is 3-bromo-2-thienyl (A36 as defined in table 36) and Y and B are as defined in each row of Table P.

Table 93 provides 15 compounds of formula (Ib) wherein A is 3-chloro-2-thienyl (A37 as defined in table 37) and Y and B are as defined in each row of Table P.

Table 94 provides 15 compounds of formula (Ib) wherein A is 2-bromo-3-thienyl (A38 as defined in table 38) and Y and B are as defined in each row of Table P.

Table 95 provides 15 compounds of formula (Ib) wherein A is 4-methyl-5thiadiazolyl(A39 as defined in table 39) and Y and B are as defined in each row of Table P.

Table 96 provides 15 compounds of formula (Ib) wherein A is 4-cyclopropyl-5-thiadiazolyl (A40 as defined in table 40) and Y and B are as defined in each row of Table P.

Table 97 provides 15 compounds of formula (Ib) wherein A is 3-methyl-4-isothiazolyl (A41 as defined in table 41) and Y and B are as defined in each row of Table P.

Table 98 provides 15 compounds of formula (Ib) wherein A is 5-methyl-4-isoxazolyl (A42 as defined in table 42) and Y and B are as defined in each row of Table P.

Table 99 provides 15 compounds of formula (Ib) wherein A is 5-cyclopropyl-4-isoxazolyl (A43 as defined in table 43) and Y and B are as defined in each row of Table P.

Table 100 provides 15 compounds of formula (Ib) wherein A is 2-(trifluoromethyl)furan-3-yl (A44 as defined in table 44) and Y, and B are as defined in each row of Table P.

Table 101 provides 15 compounds of formula (Ib) wherein A is 2-bromofuran-3-yl (A45 as defined in table 45) and Y, and B are as defined in each row of Table P.

Table 102 provides 15 compounds of formula (Ib) wherein A is 4-(trifluoromethyl)pyridazin-3-yl (A46 as defined in table 46) and Y, and B are as defined in each row of Table P.

Table 103 provides 15 compounds of formula (Ib) wherein A is 3,6-difluoro-2-(trifluoromethyl) phenyl (A47 as defined in table 47) and Y, and B are as defined in each row of Table P.

Table 104 provides 15 compounds of formula (Ib) wherein A is 2-bromo-3,6-difluorophenyl (A48 as defined in table 48) and Y, and B are as defined in each row of Table P.

Table 105 provides 15 compounds of formula (Ib) wherein A is 2-chloro-3,6-difluorophenyl (A49 as defined in table 49) and Y, and B are as defined in each row of Table P.

Table 106 provides 15 compounds of formula (Ib) wherein A is 4-(trifluoromethyl)pyrimidin-5-yl (A50 as defined in table 50) and Y, and B are as defined in each row of Table P.

Table 107 provides 15 compounds of formula (Ib) wherein A is 4-(trifluoromethyl)pyrid-3-yl (A51 as defined in table 51) and Y, and B are as defined in each row of Table P.

Table 108 provides 15 compounds of formula (Ib) wherein A is 3-(difluoromethyl)-1-methylpyrazol-4-yl (A52 as defined in table 52) and Y, and B are as defined in each row of Table P.

Table 109 provides 15 compounds of formula (Ib) wherein A is 4-methyloxazol-5-yl (A53 as defined in table 53) and Y, and B are as defined in each row of Table P.

Table 110 provides 15 compounds of formula (Ib) wherein A is 3-methoxypyrid-2-yl (A54 as defined in table 54) and Y, and B are as defined in each row of Table P.

Table 111 provides 15 compounds of formula (Ib) wherein A is 2-chlorofuran-3-yl (A55 as defined in table 55) and Y, and B are as defined in each row of Table P.

Table 112 provides 15 compounds of formula (Ib) wherein A is 2-iodofuran-3-yl (A56 as defined in table 56) and Y, and B are as defined in each row of Table P.

The compounds according to the invention can be used for controlling or destroying pests such as insects and/or fungi which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests. The compounds of formula (I) according to the invention are preventively and/or curatively valuable active ingredients in the field of pest control, even at low rates of application, which can be used against pesticide resistant pests such as insects and fungi, which compounds of formula (I) have a very favorable biocidal spectrum and are well tolerated by warm-blooded species, fish and plants. Accordingly, the present invention also makes available a pesticidal composition comprising compounds of the invention, such as formula (I).

It has now been found that the compounds of formula (I) according to the invention have, for practical purposes, a very advantageous spectrum of activities for protecting animals and useful plants against attack and damage by nematodes. Accordingly, the present invention also makes available a nematicidal composition comprising compounds of the invention, such as formula (I).

The compounds of formula (I) are especially useful for the control of nematodes. Thus, in a further aspect, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Particularly, the nematode species *Meloidogyne* spp., *Heterodera* spp., *Rotylenchus* spp. and *Pratylenchus* spp. can be controlled by compounds of the invention.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulaton auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematocides, plant activators, acaricides, and insecticides.

Accordingly, the present invention also makes available a composition comprising a compound of the invention and an agronomicaly carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

Examples of compositions for use in agriculture are emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—a compound according to the invention and the type of composition is to be selected to suit the intended aims and the prevailing circumstances.

Examples of suitable liquid carriers are unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Examples of solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Examples of foliar formulation types for pre-mix compositions are:
  GR: Granules
  WP: wettable powders
  WG: water dispersable granules (powders)
  SG: water soluble granules SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion. Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. The compounds of the present invention are particularly suited for use in soil and seed treatment applications.

In general, the pre-mix compositions of the invention contain 0.5 to 99.9 especially 1 to 95, advantageously 1 to 50,%, by mass of the desired ingredients, and 99.5 to 0.1, especially 99 to 5,%, by mass of a solid or liquid adjuvant (including, for example, a solvent such as water), where the auxiliaries (or adjuvant) can be a surfactant in an amount of 0 to 50, especially 0.5 to 40,%, by mass based on the mass of the pre-mix formulation.

A compound of the formula (I) in a preferred embodiment, independent of any other embodiments, is in the form of a plant propagation material treating (or protecting) composition, wherein said plant propagation material protecting composition may comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

Examples of application methods for the compounds of the invention and compositions thereof, that is the methods of controlling pests in the agriculture, are spraying, atomizing, dusting, brushing on, dressing, scattering or pouring—which are to be selected to suit the intended aims of the prevailing circumstances.

One method of application in agriculture is application to the foliage of the plants (foliar application), it being possible to select frequency and rate of application to match the danger of infestation with the pest/fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field. The application of the compounds of the present invention to the soil is a preferred application method.

Typical rates of application per hectare is generally 1 to 2000 g of active ingredient per hectare, in particular 10 to 1000 g/ha, preferably 10 to 600 g/ha, such as 50 to 300 g/ha.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds. The application of the compounds of the present invention to seeds is a preferred application method.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula I, which is a preferred application method, can be carried out by any known methods, such as spraying or by dusting the seeds before sowing or during the sowing/planting of the seeds.

Suitable target plants are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, amd lawn grass or turf).

In an embodiment, the plant is selected from cereals, corn, soybean, rice, sugarcane, vegetables and oil plants.

The term "plant" is to be understood as including also plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic plants are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

The following list of pesticides together with which the compounds according to the invention can be used, is intended to illustrate the possible combinations by way of example.

The following combination of the compounds of formula (I) with another active compounds are preferred (the abbreviation "TX" means a compound of the formula I, preferably a compound selected from the compounds described in Tables 1 to 112 shown above and, more preferably, Tables 116 and 118 shown below):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (995)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1395)+TX, rotenone (722)+TX, schradan (1389)+TX, sebufos (alternative name)+TX, selamectin (alternative name) [CCN]+TX, S1-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (495)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis*

(alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Pasteuria penetrans*+TX, *Pasteuria thornei*+TX, *Pasteuria nishizawae*+TX, *Pasteuria ramosa*+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3, 4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/

Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide PAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, and 3-difluoromethyl-1-methyl-1H-pyrazole-4-carboxylic acid (3',4',5'-trifluoro-biphenyl-2-yl)-amide (dislosed in WO 2006/087343)+TX.

The references in square brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright© 1995-2004]; for example, the compound "acetoprole" is described under the internet address: http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The mass ratio of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:1 to 1:100, including from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5, for example 1:3 to 3:1. The mixing ratios are understood to include, on the one hand, ratios by mass and also, on other hand, molar ratios.

The combinations of the present invention (i.e. those comprising a compound of the present invention and one or more other biological active agents) may be applied simultaneously or sequentially.

In the event, the ingredients of a combination are applied sequentially (i.e., one after the other), the ingredients are applied sequentially within a reasonable period of each other to attain the biological performance, such as within a few hours or days. The order of applying the ingredients in the combination, i.e., whether the compounds of formula (I) should be applied first or not is not essential for working the present invention.

In the event ingredients of the combinations are applied simultaneously in the present invention, they may be applied as a composition containing the combination, in which case (A) the compound of formula (I) and the one or more other ingredients in the combinations can be obtained from separate formulation sources and mixed together (known as a tank-mix, ready-to-apply, spray broth, or slurry), or (B) the compound of formula (I) and the one or more other ingredients can be obtained as single formulation mixture source (known as a pre-mix, ready-mix, concentrate, or formulated product).

In an embodiment, independent of other embodiments, a compound according to the present invention is applied as a combination. Accordingly, the present invention also provides a composition comprising a compound according the invention as herein described and one or more other biological active agents, and optionally one or more customary formulation auxiliaries; which may be in the form of a tank-mix or pre-mix composition.

The compounds of formula (I) are particularly useful for controlling and preventing helminth and nematode endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of invention are especially useful for the control of helminths and nematodes. Examples for helminths are members of the class Trematoda, commonly known as flukes or flatworms, especially members of the genera *Fasciola, Fascioloides, Paramphistomu, Dicrocoelium, Eurytrema, Ophisthorchis, Fasciolopsis, Echinostoma and Paragonimus*. Nematodes which can be controlled by the formula (I) compounds include the genera *Haemonchus, Ostertagia, Cooperia, Oesphagastomu, Nematodirus, Dictyocaulus, Trichuris, Dirofilaria, Ancyclostoma, Ascaria* and the like.

For oral administration to warm-blooded animals, the compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with about 0.01 mg/kg to 100 g/kg of animal body weight per day of the compound of the invention.

Alternatively, the compounds of the invention may be administered to animals parenterally, for example, by intraruminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compounds of the invention may be transdermally administered to animals. For parenteral administration, the dosage form chosen should provide the animal with about 0.01 mg/kg to 100 mg/kg of animal body weight per day of the compound of the invention.

The compounds of the invention may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound of the invention. In addition, the compounds of the invention may be formulated as ear tags for animals, particularly quadrupeds such as cattle and sheep.

In an embodiment, independent of any other embodiments, a compound of formula (I) is a anti-helminth compound.

In an embodiment, independent of any other embodiments, a compound of formula (I) is a pesticidal compound, preferably a nematicidal compound.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections. The following Examples serve to illustrate the invention. They do not limit the invention.

Temperatures are given in degrees Celsius; mixing ratios of solvents are given in parts by volume.

PREPARATION EXAMPLES

Example P1: Preparation of Racemic Cis N-[(2-(5-fluoro-2-pyridyl)oxetan-3-yl]-2-(trifluoromethyl)benzamide

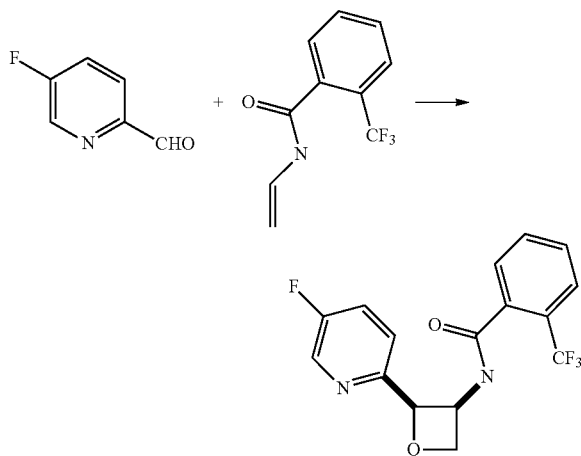

A solution of 5-fluoropyridine-2-carbaldehyde (1.163 g, 9.29 mmol) and 2-(trifluoromethyl)-N-vinyl-benzamide (2.0 g, 9.29 mmol) in acetonitrile (20 ml) was irradiated in a Rayonet reactor with 300 nm light. After 16 hours irradiation the solvent was evaporated to obtain 3.05 g of crude product, which was chromatographed on silica gel with a gradient of ethyl acetate/hexane to yield 970 mg of crude product, which was chromatographed again with a gradient of ethyl acetate/hexane to yield racemic cis N-[2-(5-fluoro-2-pyridyl)oxetan-3-yl]-2-(trifluoromethyl)benzamide as a gum.

$^1$H NMR (CDCl3, 400 MHz) δ 4.78 (dd, J=7 & 7); 5.16 (dd, J=7 & 7) (together CH2O); 5.67 (dddd, 7 & 7 & 7 & 7, CH—N); 5.97 (d, J=7, HC-pyridine); 7.03 (br d, J=7, NH) 7.2-7.7 (6H, aromatic), 8.50 (1H, s)

Example P2: Racemic cis N-[(2-(3-methyl-2-thienyl)cyclobutyl]-2-(trifluoromethyl)benzamide

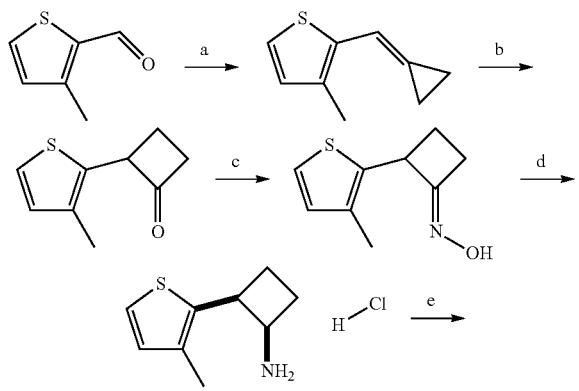

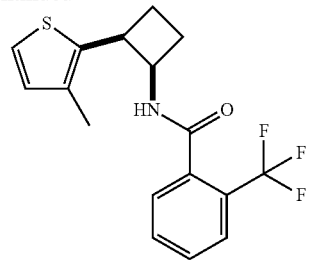

Step a. Preparation of 2-(cyclopropylidenemethyl)-3-methyl-thiophene

To a suspension of (3-bromopropyl)triphenylphosphonium bromide (20.8 g, 44.0 mmol) in anhydrous THF (140 mL) was added potassium t-butoxide (10.1 g, 88.0 mmol) in 4 separate portions 15 minutes apart. The mixture was then heated to reflux for 10 minutes, and 3-methylthiophene-2-carbaldehyde (4.79 mL, 40.0 mmol) in anhydrous THF (10 mL) was added dropwise, then continued at reflux for 4 hours. The reaction mixture was cooled down to room temperature, diluted with hexanes and filtered through a Celite pad. The filtrate was concentrated, and the residue was purified by column chromatography on silica gel (hexanes), affording 2-(cyclopropylidenemethyl)-3-methyl-thiophene as a light yellow oil.

$^1$H NMR (300 MHz, CDCl$_3$) δ 7.06 (d, 1H), 6.98-6.93 (m, 1H), 6.81 (d, 1H), 2.28 (s, 3H), 1.35-1.23 (m, 4H) ppm.

Step b. Preparation of racemic 2-(3-methyl-2-thienyl)cyclobutanone

To a solution of 2-(cyclopropylidenemethyl)-3-methyl-thiophene (3.71 g, 24.7 mmol) in CH$_2$Cl$_2$ (125 mL) was added m-chloroperbenzoic acid (ca. 75%, 5.69 g, 24.7 mmol) at 0° C. After stirring at 0° C. for 3 hours, the reaction mixture was washed with saturated NaHCO$_3$ aqueous solution and brine, dried over Na$_2$SO$_4$ and concentrated.

To the crude product in CH$_2$Cl$_2$ (85 mL) was added a 10% HBF$_4$ aqueous solution (49 mL). After stirring at room temperature for 16 hours, the mixture was extracted with CH$_2$Cl$_2$, washed with saturated NaHCO$_3$ aqueous solution and brine, dried over Na$_2$SO$_4$ and concentrated. The residue was purified by column chromatography on silica gel (hexanes:EtOAc 9:1), affording 2-(3-methyl-2-thienyl)cyclobutanone as a yellow oil.

$^1$H NMR (300 MHz, CDCl3) δ 7.09 (d, 1H), 6.83 (d, 1H), 4.72 (ddt, 1H), 3.24 (dddd, 1H), 3.08 (dddd, 1H), 2.69-2.52 (m, 1H), 2.25-2.09 (m, 4H) ppm.

Step c. Preparation of racemic (E/Z) mixture of 2-(3-methyl-2-thienyl)cyclobutanone oximes To a solution of 2-(3-methyl-2-thienyl)cyclobutanone (3.05 g, 18.4 mmol) in methanol (36 mL), sodium acetate (1.71 g, 20.2 mmol) and hydroxylamine hydrochloride (1.42 g, 20.2 mmol) were added. The mixture was stirred at room temperature for 1.5 hours. The reaction mixture was concentrated. To the crude material was added water (100 mL) and the oximes were isolated by extraction with dichloromethane (2×100 mL). The organic layer was finally washed with brine, dried over Na$_2$SO$_4$ and concentrated. The residue was purified by column chromatography on silica gel (hexanes:Et₂O 1:1), affording a racemic mixture of (E)- and (Z)-2-(3-methyl-2-thienyl)cyclobutanone oximes as a white solid.

¹H NMR (300 MHz, CDCl₃) Major isomer δ 7.08 (d, 1H), 6.93 (s, 1H), 6.80 (d, 1H), 4.63 (m, 1H), 3.08 (m, 1H), 2.93 (dd, 1H), 2.57 (m, 1H), 2.19 (s, 3H), 2.17 (m, 1H).

Step d. Preparation of Racemic Cis 2-(3-methyl-2-thienyl)cyclobutanamine hydrochloride To a solution of racemic (E/Z) mixture of 2-(3-methyl-2-thienyl)cyclobutanone oximes (1.80 g, 9.93 mmol) in methanol (40 mL) was added nickel chloride hexahydrate (118 mg, 0.50 mmol) and the mixture was cooled to −10° C. Sodium borohydride (0.77 g, 19.9 mmol) was added in small portions during 1 hour. After stirring for 30 minutes at −10° C. the reaction mixture was allowed to warm slowly to room temperature overnight. The reaction mixture was concentrated. To the crude material was added water (100 mL), then it was basified with 1M NaOH aqueous solution (ca. 14 mL) and the amine was isolated by extraction with dichloromethane (2×100 mL). The organic layer was washed with water and brine, dried over Na₂SO₄ and concentrated. The residue was purified by column chromatography on silica gel (Et₂O: hexanes:Et₃N 9:3:0.1), affording the free cyclobutanamine as a light brown oil.

To a solution of this free cyclobutanamine in CH₂Cl₂ (18 mL) was added dropwise 4M HCl in dioxane (12.2 mL, 48.7 mmol) at 0° C. under inert atmosphere. The reaction mixture was stirred at room temperature for 4.5 hours. The reaction mixture was concentrated and the residue was triturated with Et₂O:CH₂Cl₂ (10:1 mL) overnight at room temperature, then the suspension was cooled down in an ice bath and a precipitate was filtered off, washed with small amount of Et₂O and dried under vacuum to give racemic cis 2-(3-methyl-2-thienyl)cyclobutanamine hydrochloride as an off-white solid.

m.p. 181° C. (with dec.)

Step e. Preparation of Racemic Cis N-[(2-(3-methyl-2-thienyl)cyclobutyl]-2-(trifluoromethyl)benzamide To the racemic cis 2-(3-methyl-2-thienyl)cyclobutanamine hydrochloride (129 mg, 0.60 mmol) and triethylamine (0.21 mL, 1.50 mmol) in anhydrous THF (5 mL) was added dropwise 2-(trifluoromethyl)benzoyl chloride (0.10 mL, 0.66 mmol) in anhydrous THF (2 mL) at 0° C. under inert atmosphere. The reaction mixture was stirred at room temperature overnight. Triethylamine hydrochloride was filtered off, washed with small amount of Et₂O. The filtrate was concentrated and purified by column chromatography on silica gel (hexanes:Et₂O 1:1), followed by purification on preparative TLC (hexanes:EtOAc 7:1), affording racemic cis N-[(2-(3-methyl-2-thienyl)cyclobutyl]-2-(trifluoromethyl)benzamide as a white solid.

m.p. 111-112° C.

Example P3: N-[2-(benzothiophen-2-yl)cyclobutyl]-2-(trifluoromethyl)benzamide

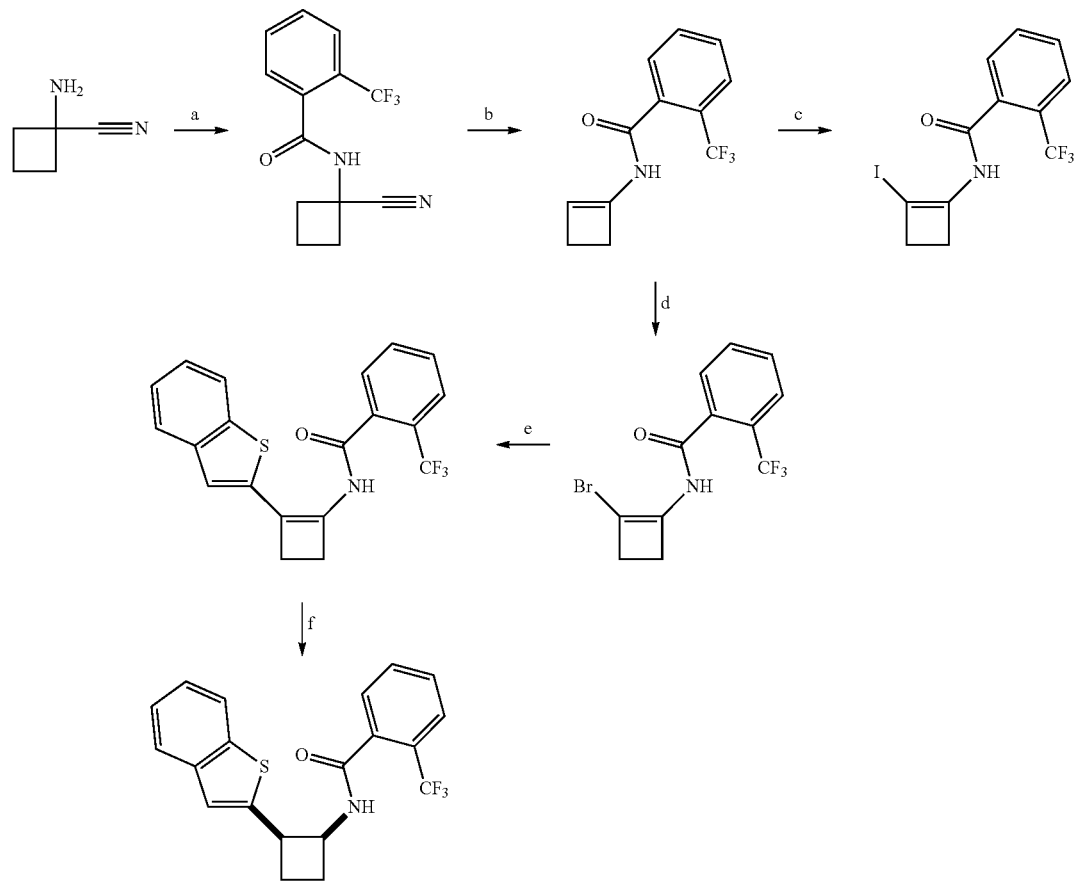

Step a. Preparation of N-(1-cyanocyclobutyl)-2-(trifluoromethyl)benzamide 1-cyanocyclobutanamine chloride (1 g, 7.54 mmol) was suspended in 10 mL of water. Sodium carbonate (1.60 g, 15.1 mmol) was added with stirring followed by 2-(trifluoromethyl)benzoyl chloride (1.57 g, 7.54 mmol). The reaction mixture was stirred for one hour and then shaken between ethyl acetate and 2M HCl, then washed with 2M sodium carbonate, and then with saturated brine. The resulting organic layer was dried over MgSO4 and concentrated. The resulting solid was triturated with cold diethylether to afford pure N-(1-cyanocyclobutyl)-2-(trifluoromethyl)benzamide. Melting point: 148-154° C.

$^1$H NMR (CDCl3, 400 MHz) δ 7.75 (d, J=10 Hz, 1H), 7.60 (m, 3H), 6.15 (br s, 1H), 2.9 (m, 2H), 2.5 (m, 1H), 2.2 (m, 2H) ppm

Step b. Preparation of N-(cyclobuten-1-yl)-2-(trifluoromethyl)benzamide

N-(1-cyanocyclobutyl)-2-(trifluoromethyl)benzamide (268 mg, 1 mmol) was dissolved in 1 ml of dry THF in dried flask under argon. tBuONa (2M in THF) (0.75 ml, 0.5 mmol) was then added and stirred at room temperature for four days. The reaction was diluted with tBuOMe and then quenched with 1M solution of NaHCO3, followed by a solution of saturated brine. The resulting organic layer was dried over MgSO4, filtered and concentrated to afford 245 mg of crude material, which was chromatographed on silica to obtain pure N-(cyclobuten-1-yl)-2-(trifluoromethyl)benzamide. Melting point: 129-133° C.

$^1$H NMR (CDCl3, 400 MHz) δ 7.75 (d, J=10 Hz, 1H), 7.6 (m, 3H), 7.15 (br s, 1H), 5.6 (s, 1H), 2.8 (m, 2H), 2.45 (m, 2H) ppm

Step c. Preparation of N-(2-iodocyclobuten-1-yl)-2-(trifluoromethyl)benzamide N-(cyclobuten-1-yl)-2-(trifluoromethyl)benzamide (15 mg, 0.0622 mmol) was dissolved in 0.200 ml dichloromethane. Triethylamine (0.0105 mL, 0.0746 mmol, 7.63 mg) was added. Under stirring N-iodosuccinimide (14.4 mg, 0.0622 mmol) was added. It dissolved quickly. TLC (50% EtOAc/cyclohexane) after 10 minutes at RT showed complete reaction. The reaction mixture was shaken between tBuOMe and 1M NaHCO3, dried with MgSO4, and evaporated. Chromatography on silica with a 0 to 50% EtOAc/cyclohexane gradient gave pure N-(2-iodocyclobuten-1-yl)-2-(trifluoromethyl)benzamide.

1H-NMR (CDCl3) 2,78 (2H, t); 3.42 (2H, t); 7.20 (br s, NH); 7.61 (3H, m); 7.73 (1H, s).

Step d. Preparation of N-(2-bromocyclobuten-1-yl)-2-(trifluoromethyl)benzamide N-(cyclobuten-1-yl)-2-(trifluoromethyl)benzamide (3.86 g, 16 mmol) was stirred in dichloromethane (ca 30 ml) at ca 10° C. Na2CO3 (2M aq., ca 20 ml) was added and iPr2NEt (2.09 g, 16 mmol, 2.82 ml) was added, followed by N-bromosuccinimide (2.85 g). The organic phase was then dried with MgSO4, and evaporated to give the crude product, which was chromatographed on 120 g silica with a gradient of 0 to 50% EtOAc in cyclohexane to yield N-(2-bromocyclobuten-1-yl)-2-(trifluoromethyl)benzamide. M.p. 112-113-5° C.

$^1$H NMR (300 MHz, CDCl$_3$) δ 7.74 (d, 1H), 7.60 (m, 3H), 7.28 (br s, 1H), 3.21 (t, 2H), 2.78 (t, 2H) ppm

Step e. N-[2-(benzothiophen-2-yl)cyclobuten-1-yl]-2-(trifluoromethyl)benzamide (89-1)

To a solution of N-(2-bromocyclobuten-1-yl)-2-(trifluoromethyl)benzamide (60 μmol) in THF (0.7 ml) was added successively benzothiophen-2-ylboronic acid (120 μmol), a solution of potassium phosphate (25.5 mg) in water (0.3 ml) and a solution of chloro(2-dicyclohexylphosphino-2',4',6'-triisopropyl-1,1'-biphenyl)[2-(2'-amino-1,1-biphenyl)]palladium(II) (4.7 mg; 6 μmol) in THF (0.2 ml). The reaction mixture was flushed with argon and stirred at 110° C. for 30 minutes in a microwave oven. Then the THF was evaporated. The crude mixture was diluted with ethyl acetate (2 ml), washed 3 times with water (2 ml) and the organic phase was concentrated. The crude material was purified via chromatography to give N-[2-(benzothiophen-2-yl)cyclobuten-1-yl]-2-(trifluoromethyl)benzamide.

This method was used to prepare all compounds from Table 115, except compounds 115-30 to 115-34.

Step f. N-[2-(benzothiophen-2-yl)cyclobutyl]-2-(trifluoromethyl)benzamide (90-24)

To a solution of N-[2-(benzothiophen-2-yl)cyclobuten-1-yl]-2-(trifluoromethyl)benzamide. (22.3 mg) in methanol (2 ml) was added (1,1'-bis(di-i-propylphosphino)ferrocene(1, 5'-cyclooctadiene)rhodium (I) tetrafluoroborate (4.3 mg) under inert atmosphere. The reaction mixture was placed in a stainless steel autoclave and was hydrogenated at 50 bar and ambient temperature for 22 hours. The crude mixture was concentrated. The crude material was purified via chromatography to give N-[2-(benzothiophen-2-yl)cyclobutyl]-2-(trifluoromethyl)benzamide 1H-NMR (CDCl3, 400 MHz): 7.80-7.05 (m, 9H), 5.75 (d, 1H), 5.04 (m, 1H), 4.25 (m, 1H), 2.65 (m, 1H), 2.45 (m, 1H), 2.25 (m, 2H) ppm.

This method was used to prepare Compound Nos. 116-24 to 116-35 and 116-44 to 116-48 of Table 116.

Example P4: Preparation of N-(cyclobuten-1-yl)-2-(trifluoromethyl)benzamide

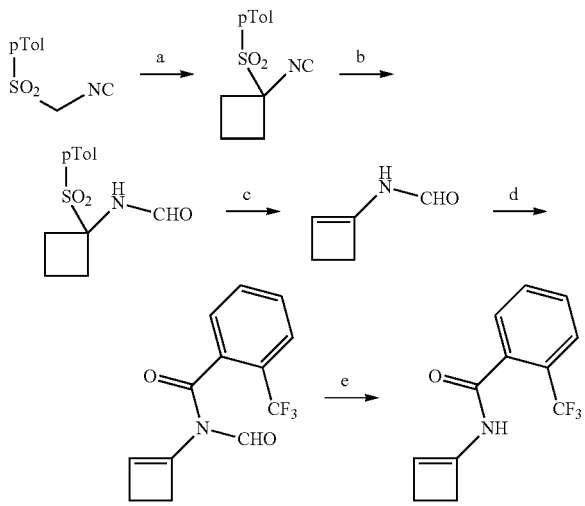

Step a. Preparation of 1-isocyano-1-(4-methylphenyl)sulfonyl-cyclobutane

Sodium hydride (3.1 g, 57% in oil, 74 mmol) was washed with hexane under argon. A 3:1 mixture of DMSO and diethyl ether (50 ml) was added. This was stirred well and a solution of 1,3-dibromopropane (3.1 ml, 6.1 g, 31 mmol) and 1-(isocyanomethylsulfonyl)-4-methyl-benzene (5.0 g, 26 mmol) in a 3:1 mixture of DMSO and diethyl ether (30 ml) was added dropwise, causing an exotherm to 43° C. The addition took about 30 minutes. After one hour stirring a precipitate of NaBr came out, and the temperature sank to RT. Water (60 ml) was slowly added, and the crude mixture extracted with diethylether, which was then dried with Na2SO4 and evaporated down to give the crude material. This was stirred with ether, cooled in an ice bath, and the crystals filtered off to yield 1-isocyano-1-(4-methylphenyl)sulfonyl-cyclobutane as light coloured crystals.

M.p. 94-97° C.

Step b. Preparation of N-(1-(4-methylphenyl)sulfonylcyclobutyl)formamide

Hydrochloric acid (19 ml, 2M, 36 mmol) as added to a solution of 1-(1-isocyanocyclobutyl)sulfonyl-4-methyl-benzene (8.5 g, 36 mmol) in THF (50 ml) at 0-5° C. which was cooled in an ice-water bath. After TLC in 50% EtOAc in hexane showed complete reaction, NaHCO3 (1M) was added to make the mixture lightly basic. The mixture was extracted with tBuOMe, dried with Na2SO4, and evaporated to give the crude product, which was stirred in ether and left in the refrigerator at ca 0 to 5° C. The resulting solid was filtered off to yield N-(1-(4-methylphenyl)-sulfonyl-cyclobutyl)formamide as beige crystals.

M.p. 83-88° C.

Step c. Preparation of N-(cyclobuten-1-yl)formamide

A solution of N-[1-(p-tolylsulfonyl)cyclobutyl]formamide (500 mg, 1.97 mmol) in THF (3 ml) was cooled to 0° C. under argon. A solution of NaOtBu in THF (2.96 ml, 2M, 5.92 mmol, 3 equiv.) was added slowly. After 30 minutes at 0° C. the mixture was extracted between diethylether and NaHCO3 (aq). And the ether phase evaporated to yield N-(cyclobuten-1-yl)formamide as an oil. 1H-NMR showed a mixture of rotamers.

$^1$H NMR (300 MHz, CDCl$_3$) δ 8.33 (d, 1H), 8.19 (s, 1H), 5.45 (s, 1H), 5.05 (s, 1H), 2.73 (m, 2H), 2.38 (m, 2H).

Step d. Preparation of N-(cyclobuten-1-yl)-N-formyl-2-(trifluoromethyl)benzamide A solution of N-(cyclobuten-1-yl)formamide (190 mg, 1.956 mmol) in ether and THF as a solution obtained as above before evaporation was cooled to 0° C. Et3N (300 mg, 2.935 mmol) and DMAP (23.9 mg, 0.1956 mmol) were added then 2-(trifluoromethyl)benzoyl chloride (449 mg, 2.152 mmol) was added dropwise. There was an exotherm to 7° C. and a precipitate came out of solution. The cool bath was removed and the mixture stirred for 2 hours then shaken between EtOAc and NaHCO3 (aq.), washed with brine, dried with Na2SO4, and evaporated to give N-(cyclobuten-1-yl)-N-formyl-2-(trifluoromethyl)benzamide as a crude product $^1$H NMR (300 MHz, CDCl$_3$) δ 8.88 (s, 1H), 5.82 (s, 1H), 2.83 (t, 2H), 2.38 (t, 2H)

Step e. Preparation of N-(cyclobuten-1-yl)-2-(trifluoromethyl)benzamide

N-(cyclobuten-1-yl)-N-formyl-2-(trifluoromethyl)benzamide (63 mg, 0.26 mmol) was dissolved in THF (1 ml) and cooled to 0° C. NaOH (2M, 1.2 equiv.) was added and stirred for 30 min at 0° C., then shaken between EtOAc and water, dried with Na2SO4, and evaporated to yield crude N-(cyclobuten-1-yl)-2-(trifluoromethyl)benzamide $^1$H NMR (CDCl3, 400 MHz) δ 7.75 (d, J=10 Hz, 1H), 7.6 (m, 3H), 7.15 (br s, 1H), 5.6 (s, 1H), 2.8 (m, 2H), 2.45 (m, 2H) ppm

Example P5: Preparation of N-(2-iodocyclobuten-1-yl)formamide

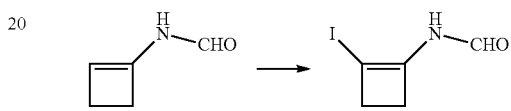

A solution of N-(cyclobuten-1-yl)formamide (82 mg, 0.8443 mmol) in ether and THF prepared as described above in example P3 was cooled to 0° C. A solution of K2CO3 (0.844 ml, 1.689 mmol, 2M, aq.) was added and iPr2NEt (109 mg, 0.8443 mmol) was added. Under stirring iodine (214 mg, 0.8443 mmol) was added. After performing a TLC examination with 50% EtOAc/cyclohexane the mixture was shaken between EtOAc and water, washed with NaS2O3 (aq.), then HCl (aq), then NaHCO3 (aq), then brine. It was dried with Na2SO4, and evaporated to give crude product, which was chromatographed on silica with EtOAc/cyclohexane to yield N-(2-iodocyclobuten-1-yl)formamide $^1$H NMR (CDCl3, 400 MHz, mixture of two rotamers) δ 8.43 (d, 1H), 8.18 (s, 1H), 3.30 (t, 2H), 3.00 (t, 2H), 2.74 (m, 2H).

Example P6: Preparation N-(cyclobuten-1-yl)-4-methoxy-benzamide

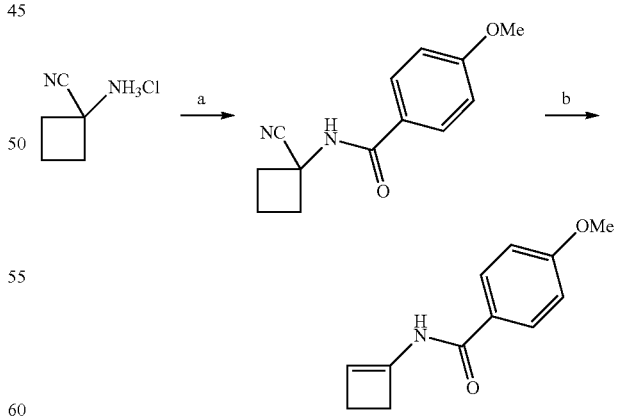

Step a. Preparation of N-(1-cyanocyclobutyl)-4-methoxy-benzamide 1-cyanocyclobutanamine hydrochloride (200 mg, 1.5084 mmol) was dissolved in THF, the solution was then cooled down to 0° C. Et3N (305 mg, 3.0168 mmol) was then added and stirred for 15 min. 4-methoxybenzoyl chloride (257 mg., 1.5084 mmol) was then added and the reaction mixture warmed up to room temperature. After 17 hours the mixture is a suspension. It was shaken between EtOAc and water, washed with NaHCO3 (1M, aq) and brine, dried over MgSO4 and evaporated to yield 255 mg of crude product, which was chromatographed on silica with EtOAc/cyclohexane to afford N-(1-cyanocyclobutyl)-4-methoxy-benzamide as a white solid. 1H NMR (CDCl3, 400 MHz) δ 7.75 (d, J=10 Hz, 2H), 6.95 (d, J=10 Hz, 2H), 6.38 (br s, 1H), 2.9 (m, 2H), 2.5 (m, 1H), 2.3 (m, 1H), 2.15 (m, 1H)

Step b. Preparation of
N-(cyclobuten-1-yl)-4-methoxy-benzamide

A solution of NaOtBu in THF (0.938 ml, 2M, 1.876 mmol) was added to a solution of N-(1-cyanocyclobutyl)-4-methoxy-benzamide (144 mg, 0.6253 mmol) in THF (3 ml). After 24 hours at RT the mixture was shaken between tBuOMe and NaHCO3 (1M, aq.), dried with MgSO4 and the solvent evaporated to afford crude product, which was chromatographed on silica to afford N-(cyclobuten-1-yl)-4-methoxy-benzamide as a white solid.

M.p. 79-85° C.

$^1$H NMR (CDCl$_3$, 400 MHz) δ 7.75 (d, J=10 Hz, 2H), 7.5 (br s, 1H), 6.95 (d, J=10 Hz, 2H), 3.85 (s, 3H), 2.8 (m, 2H), 2.45 (m, 2H).

Example P7: Preparation
N-(cyclobuten-1-yl)acetamide

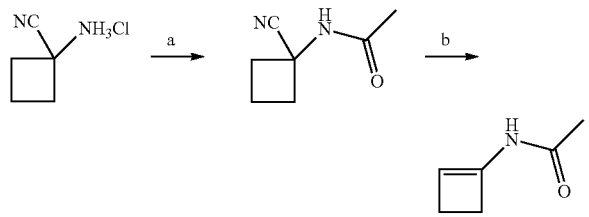

Step a. Preparation of
N-(1-cyanocyclobutyl)acetamide

Prepared according to example P3 step a to afford N-(1-cyanocyclobutyl)acetamide as a brown solid. Melting point: 70-72° C.

1H NMR (CDCl3, 400 MHz) δ 5.85 (br s, 1H), 2.7 (m, 2H), 2.3 (m, 2H), 2.15 (m, 1H), 2.05 (m, 1H), 1.95 (s, 3H)

Step b. Preparation of
N-(cyclobuten-1-yl)acetamide

Prepared according to example P3 step b to afford N-(cyclobuten-1-yl)acetamide as a pale yellow solid.

1H NMR (CDCl3, 400 MHz) δ 6.98 (br s, 1H), 5.40 (s, 1H), 2.68 (t, 2H), 2.48 (m, 2H), 2.01 (s 3H)

Example P8: Preparation of Racemic Cis N-[2-(2-pyridyl)cyclobutyl]-2-(trifluoromethyl) benzamide

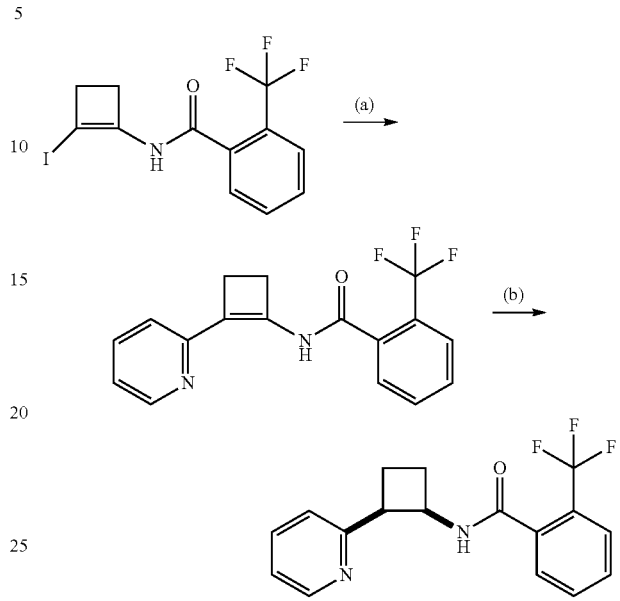

Step a. Preparation of N-[2-(2-pyridyl)cyclobuten-1-yl]-2-(trifluoromethyl)benzamide N-(2-iodocyclobuten-1-yl)-2-(trifluoromethyl)benzamide (0.272 mmol, 0.100 g) was introduced in a 25 ml three-neck round-bottom flask and dissolved in anhydrous tetrahydrofuran (5 ml). The reaction mixture was flushed three times with vacuum/argon cycles and submitted to an argon atmosphere. Palladium(II) acetate (0.00535 mmol, 0.00120 g) and XPhos (2-Dicyclohexylphosphino-2',4',6'-triisopropylbiphenyl, 0.0108 mmol, 0.00520 g) were added in one share, then freshly opened 2-pyridylzinc bromide in THF (0.5M; 0.409 mmol, 0.8 g, 0.8 ml) was added drop-wise. The reaction mixture was stirred at room temperature overnight (21 hours), then at 50° C. during 5 hours. Additional 2-pyridylzinc bromide in THF (0.5M; 0.136 mmol, 0.27 ml) was added and the reaction mixture was stirred at 50° C. overnight (18 hours). At this state the conversion of the starting material was total. The reaction mixture was cooled down to room temperature, quenched by pouring it on water and extracted twice with ethyl acetate. Organic layers were combined, dried with anhydrous sodium sulfate, filtered and concentrated to give a dark oil. The crude mixture was purified by chromatography to afford a brownish sticky oil.

1H NMR (CDCl3, 400 MHz) δ 9.94 (1H, br. s.), 8.31-8.45 (1H, m), 7.53-7.81 (5H, m), 6.91-7.03 (2H, m), 3.34 (2H, t), 2.73, (2H, t).

Step b. Preparation of Racemic Cis N-[2-(2-pyridyl)cyclobutyl]-2-(trifluoromethyl) benzamide Prepared according to example P3 step f to afford a pale yellow gum.

LCMS characterization in table 116 (compound 116-49).

Example P9: Preparation of Racemic Cis N-[2-(3-chloro-2-pyridyl)cyclobutyl]-2-(trifluoromethyl) benzamide

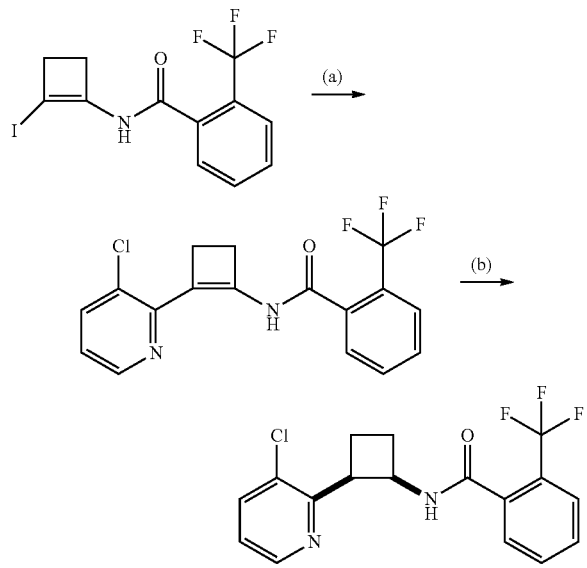

Step a. Preparation of N-[2-(3-chloro-2-pyridyl)cyclobuten-1-yl]-2-(trifluoromethyl)benzamide N-(2-iodocyclobuten-1-yl)-2-(trifluoromethyl)benzamide (0.817 mmol, 0.300 g) and tributyl-(3-chloro-2-pyridyl)stannane (1.02 mmol, 0.411 g) were introduced in a 25 ml round-bottom flask and dissolved in anhydrous and degassed N,N-dimethylformamide (2 ml). In a separate 10 ml round bottom flask was introduced anhydrous and degassed N,N-dimethylformamide (3 ml). Palladium(II) chloride diacetonitrile complex (0.204 mmol, 0.0539 g), copper (I) iodide (0.817 mmol, 0.156 g, 0.0277 ml) and triphenylarsine (0.817 mmol, 0.250 g) were added subsequently in one share and the mixture was stirred under an argon atmosphere for 2 minutes. The mixture turned dark just after the addition of copper (I) iodide. The catalyst solution was then added drop-wise to the reaction mixture flask under an argon atmosphere. The reaction mixture was stirred at room temperature under an argon atmosphere overnight (18 hours). The reaction mixture was diluted in ethyl acetate, filtered through Celite and a small layer of silica. This organic solution was washed with water to remove a part of DMF, then washed with an aqueous potassium fluoride solution. The organic layer was dried with anhydrous sodium sulfate, filtered and concentrated to give a dark solid. The crude mixture was purified by chromatography to give an orange solid which was triturated with a small volume of cyclohexane. An orange solid was obtained.

1H NMR (CDCl3, 400 MHz) δ 10.35 (br. s., 1H) 8.25 (d, 1H) 7.77 (d, 1H) 7.55-7.73 (m, 4H) 6.91 (dd, 1H), 3.33 (m, 2H) 3.11 (t, 2H).

This method was used to prepare Compound Nos. 115-31 to 115-33 of Table 115.

Step b. Preparation of Racemic Cis N-[2-(3-chloro-2-pyridyl)cyclobutyl]-2-(trifluoromethyl) benzamide Prepared according to example P3 step f except the fact that the reaction time was extended to 51 hours. A colourless viscous oil was obtained.

1H NMR (CDCl3, 400 MHz) δ 8.38 (dd, 1H) 7.78 (d, 1H) 7.69 (dd, 1H) 7.61-7.67 (m, 1H) 7.45-7.55 (m, 2H) 7.29-7.36 (m, 1H) 7.12 (dd, 1H) 5.06-5.28 (m, 1H) 4.35-4.52 (m, 1H) 2.48-2.63 (m, 1H) 2.28-2.44 (m, 2H) 2.13-2.24 (m, 1H)

This method was used to prepare Compound Nos. 116-50 and 116-51.

Example P10: Preparation of N-[(1S,2R)-2-(3-chloro-2-pyridyl)cyclobutyl]-2-(trifluoromethyl) benzamide

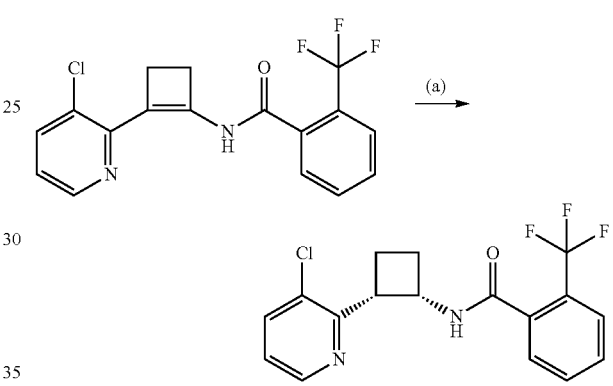

(R)-1-[(S)-2-(Di-tert.-butylphosphino)ferrocenyl]ethyl-di-2-methylphenylphosphine (SL-J505-1, 0.0427 mmol, 0.0251 g) and bis(1,5-cyclooctadiene)rhodium(I) trifluoromethanesulfonate (0.0388 mmol, 0.0182 g) were weighted and transferred to a vial in an inert atmosphere. Methanol was degassed by flushing it several times with vacuum/argon cycles. Degassed methanol (7 ml) was then introduced in a 25 ml round-bottom flask containing N-[2-(3-chloro-2-pyridyl)cyclobuten-1-yl]-2-(trifluoromethyl)benzamide (0.388 mmol, 0.137 g), followed by the addition of both catalyst and ligand, and the reaction mixture was stirred at room temperature under an argon atmosphere until the reaction mixture becomes homogeneous (15 minutes). The solution was then canulated into a 100 ml autoclave previously inerted with argon. The autoclave was tightly closed and submitted to hydrogen pressure (50 bar) at 50° C. overnight (17 hours). The autoclave was cooled down, inerted with argon, and opened. The reaction mixture was filtered through Celite and a small layer of silica, washed with methanol and concentrated to give a brownish solid. The crude mixture was purified by chromatography to afford an orange viscous oil: It was analysed via chiral HPLC (method F) which showed an ee of 33% in favour of the desired enantiomer eluting at 4.66 min (minor enantiomer eluting at 6.38 min).

1H NMR (CDCl3, 400 MHz) δ 8.38 (dd, 1H) 7.78 (d, 1H) 7.69 (dd, 1H) 7.61-7.67 (m, 1H) 7.45-7.55 (m, 2H) 7.29-7.36 (m, 1H) 7.12 (dd, 1H) 5.06-5.28 (m, 1H) 4.35-4.52 (m, 1H) 2.48-2.63 (m, 1H) 2.28-2.44 (m, 2H) 2.13-2.24 (m, 1H)

Example P11: Preparation of Racemic Cis N-[2-(3,5-dichloro-2-pyridyl)cyclobutyl]-2-(trifluoromethyl)benzamide

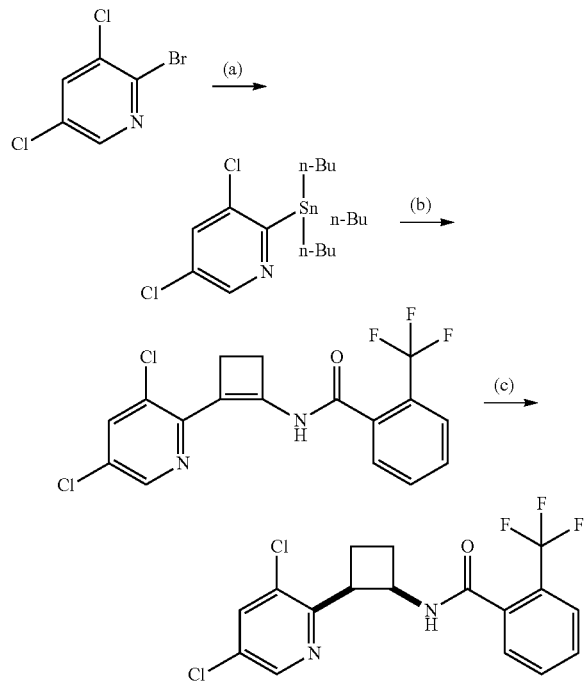

Step a. Preparation of tributyl-(3,5-dichloro-2-pyridyl)stannane 2-bromo-3,5-dichloro-pyridine (2.20 mmol, 0.500 g) was introduced in a 50 ml three-neck round-bottom flask and dissolved in anhydrous tetrahydrofuran (10 ml). The reaction mixture was flushed three times with vacuum/argon cycles, submitted to an argon atmosphere and cooled down to −78° C. with an acetone/dry ice slurry. At −78° C., n-butyllithium in hexane (1.6M; 2.42 mmol, 1.5 ml) was then added drop-wise within 5 minutes. The reaction mixture was stirred at −78° C. during 1 hour. Then tributyl (chloro)stannane (2.64 mmol, 0.861 g, 0.717 ml) was added and the cold bath was removed. The reaction mixture was stirred during 1 hour whereupon it slowly went back to room temperature. The reaction mixture was quenched with saturated ammonium chloride solution and extracted twice with ethyl acetate. Organic layers were combined, dried with anhydrous sodium sulfate, filtered and concentrated to give a dark liquid. The crude mixture was purified by chromatography to afford a pale yellow liquid which was characterized as the desired product.

1H NMR (CDCl3, 400 MHz) δ 8.34-8.37 (m, 2H) 1.50-1.60 (m, 6H) 1.32-1.40 (m, 6H) 1.28-1.32 (m, 6H) 0.90 (t, 9H).

Step b. Preparation of N-[2-(3,5-dichloro-2-pyridyl)cyclobuten-1-yl]-2-(trifluoromethyl) benzamide Prepared according to example P9 step a except the fact that the reaction time was shortened to 3 hours to afford an amber viscous oil.

1H NMR (CDCl3, 400 MHz) δ 8.41 (s, 2H) 7.74 (d, 1H) 7.56-7.67 (m, 3H) 7.47 (br. s., 1H) 3.25 (t, 2H) 2.99 (t, 2H).

Step c. Preparation of Racemic Cis N-[2-(3,5-dichloro-2-pyridyl)cyclobutyl]-2-(trifluoromethyl)benzamide To (R)-1-[(S$_P$)-2-(Diphenylphosphino)ferrocenyl]ethyldi-tert-butylphosphine (SL-J002-1, 2.4 mg, 0.03 eq.) and (S)-1-[(R$_P$)-2-(Diphenylphosphino)ferrocenyl]ethyldi-tert-butylphosphine Josiphos (SL-J002-2, 2.4 mg, 0.03 eq.) was added carefully degassed MeOH (1.5 ml). The suspension was stirred for 10 min at r.t. under argon and then Ru(COD)(OOCCF$_3$)$_2$ dimer hydrate (3.2 mg, 0.05 eq.) was added. The suspension was stirred for 15 more minutes under argon. The reaction mixture became homogeneous. This yellow solution was added to N-[2-(3,5-dichloro-2-pyridyl)cyclobuten-1-yl]-2-(trifluoromethyl) benzamide (28 mg, 1 eq.). The reaction mixture was stirred 20 minutes under argon. It was then transferred to a 100 ml autoclave under argon atmosphere. The autoclave was tightly closed, purged with hydrogen and put under 50 bars of hydrogen. It was then heated to 50° C. with stirring (1000 rpm) for 3 days. The autoclave was cooled down to r.t. purged with argon, the reaction mixture was concentrated under vacuum (40° C., 30 mbar). The crude material was purified via chromatography.

LCMS characterization in table 116 (compound 116-61).

Example P11: Preparation of N-[2-[3-chloro-5-(trifluoromethyl)-2-pyridyl]cyclobuten-1-yl]-2-(trifluoromethyl)benzamide

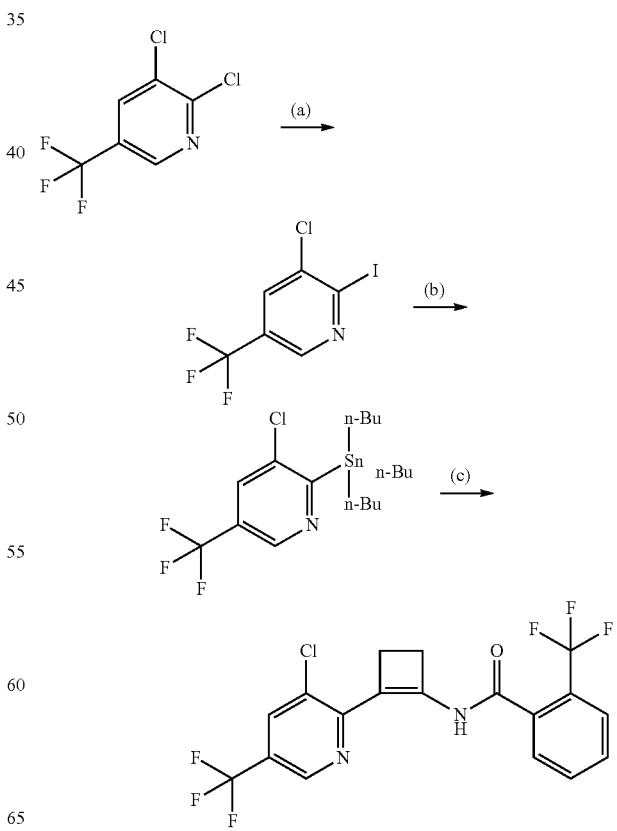

Step a. Preparation of
3-chloro-2-iodo-5-(trifluoromethyl)pyridine 2,3-dichloro-5-(trifluoromethyl)pyridine (11.8 g, 54.6 mmol) was dissolved in acetonitrile (80 ml), then sodium iodide (12.4 g, 81.9 mmol) was added in one portion. Acetyl chloride (5.89 ml, 81.9 mmol) was added slowly. The white suspension turned to intensive yellow and the reaction mixture was stirred at reflux for 4 hours. It turned into a dark brown suspension. The reaction mixture was concentrated under vacuum and purified by silica gel chromatography to give a colourless oil.
1H NMR (CDCl3, 400 MHz) δ 8.52 (d, 1H), 7.87 (d, 1H).

Step b. Preparation of tributyl-[3-chloro-5-(trifluoromethyl)-2-pyridyl]stannane 3-chloro-2-iodo-5-(trifluoromethyl)pyridine (1.7 g, 5.5 mmol) was dissolved in dry toluene (8 ml) and cooled down to −75° C. Butyl lithium in hexanes (1.6M; 5.5 mmol, 3.5 ml) were added slowly via a syringe to give a slightly yellow solution. The reaction mixture was stirred at −75° C. for 1 hour. The solution became dark green. Tributyltin chloride (6.1 mmol, 1.6 ml) was added slowly at −75° C. and the mixture was slowly warmed up to room temperature. The reaction mixture was poured into saturated aqueous NH4Cl solution (50 ml) and extracted with tBuOMe, dried with Na2SO4 and evaporated to give a dark mixture which was purified by silica gel chromatography to give the desired product as a colourless oil.
1H NMR (CDCl3, 400 MHz) δ 8.87 (dd, 1H) 7.73 (d, 1H) 1.53-1.62 (m, 6H) 1.28-1.39 (m, 6H) 1.21-1.28 (m, 6H) 0.90 (t, 9H)

Step c. Preparation of N-[2-[3-chloro-5-(trifluoromethyl)-2-pyridyl]cyclobuten-1-yl]-2-(trifluoromethyl)benzamide Prepared according to example P9 step a except the fact that the reaction time was extended to 2 days to afford the desired product as a colourless oil.
LCMS characterization in table 115 (compound 115-34).

TABLE 113

Compounds of formula (II)

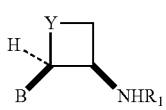

(II)

| Entry | B | Y | R1 | RT (min) | [M + H] (measured) | Method | MP (° C.) |
|---|---|---|---|---|---|---|---|
| 113-1 | 3-methyl-thien-2-yl | CH2 | H | | | | 181* |
| 113-2 | 5-chloro-thien-2-yl | CH2 | H | | | | 218* |
| 113-3 | 6-chloro-pyridin-3-yl | CH2 | H | 0.25 | 183 | A | |
| 113-4 | 4-chloro-1-methyl-1H-pyrazol-3-yl | CH2 | H | | | | 158* |
| 113-5 | 6-trifluoromethyl-pyridin-3-yl | CH2 | H | 4.79 | 217 | C | |
| 113-6 | 2-(2,2-difluoro-1,3-benzodioxol-4-yl) | CH2 | H | 0.36 | 228 | A | |
| 113-7 | 2-(6-bromo-1,3-benzodioxol-5-yl) | CH2 | H | 0.55 | 270 | A | |
| 113-8 | 5-chloro-2-furyl | CH2 | H | 0.39 | 172 | A | |

TABLE 113-continued

Compounds of formula (II)

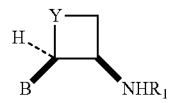

(II)

| Entry | B | Y | R1 | RT (min) | [M + H] (measured) | Method | MP (° C.) |
|---|---|---|---|---|---|---|---|
| 113-9 | 5-bromo-2-furyl | CH2 | H | | | | 206-208* |

*HCl Salt

Table 113 shows selected melting point, selected HPLC-MS, selected GC-MS and selected NMR data for compounds (II) or their hydrochloride salt of the present invention. CDCl3 was used as the solvent for NMR measurements, unless otherwise stated. No attempt is made to list all characterising data in all cases.

In Table 113 and throughout the description that follows, temperatures are given in degrees Celsius; "NMR" means nuclear magnetic resonance spectrum; HPLC is high pressure liquid chromatography; GC stands for gas chromatography, MS stands for mass spectrum; "%" is percent by weight, unless corresponding concentrations are indicated in other units. The following abbreviations are used throughout this description:
m.p.=melting point [° C.] b.p.=boiling point.
s=singlet br=broad
d=doublet dd=doublet of doublets
t=triplet q=quartet
m=multiplet ppm=parts per million

TABLE 114

Trans isomers of compounds (II)

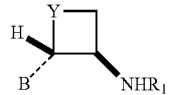

Trans isomer of (II)

| Entry | B | Y | R1 | RT (min) | [M + H] (measured) | Method |
|---|---|---|---|---|---|---|
| 114-1 | 2-(6-bromo-1,3-benzodioxol-5-yl) | CH2 | H | 0.61 | 270 | A |

TABLE 115

Compounds of formula (IX)

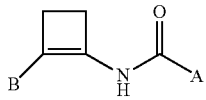

(IX)

| Entry | A | B | RT (min) | [M + H] (measured) |
|---|---|---|---|---|
| 115-1 | 2-trifluoromethylphenyl | benzothiophen-2-yl | 1.08* | 374 |
| 115-2 | 2-trifluoromethylphenyl | pyrimidin-5-yl | 0.62* | 320 |
| 115-3 | 2-trifluoromethylphenyl | benzofuran-2-yl | 1.06* | 358 |
| 115-4 | 2-trifluoromethylphenyl | 2-chloroquinol-3-yl | 1.01* | 403 |

TABLE 115-continued

Compounds of formula (IX)

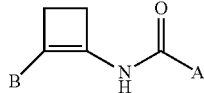

(IX)

| Entry | A | B | RT (min) | [M + H] (measured) |
|---|---|---|---|---|
| 115-5 | 2-trifluoromethylphenyl | 3-quinolyl | 0.75* | 369 |
| 115-6 | 2-trifluoromethylphenyl | 5-methylbenzothiophen-2-yl | 1.14* | 388 |
| 115-7 | 2-trifluoromethylphenyl | 2-methylindazol-5-yl | 0.77* | 372 |
| 115-8 | 2-trifluoromethylphenyl | 1-methylindazol-5-yl | 0.84* | 372 |
| 115-9 | 2-trifluoromethylphenyl | 1,3-benzothiazol-5-yl | 0.88* | 375 |
| 115-10 | 2-trifluoromethylphenyl | 2-pyrido[2,3-b]pyrazin-7-yl | 0.66* | 371 |
| 115-11 | 2-trifluoromethylphenyl | 2-methyl-1,3-benzoxazol-5-yl | 0.87* | 373 |
| 115-12 | 2-trifluoromethylphenyl | thiazol-5-yl | 0.71* | 325 |
| 115-13 | 2-trifluoromethylphenyl | 4-(trifluoromethyl)-pyrid-3-yl | 0.88* | 387 |
| 115-14 | 2-trifluoromethylphenyl | 8-quinolyl | 1.1* | 369 |
| 115-15 | 2-trifluoromethylphenyl | 1-methylindol-5-yl | 0.96* | 371 |
| 115-16 | 2-trifluoromethylphenyl | benzothiophen-3-yl | 1.05* | 374 |
| 115-17 | 2-trifluoromethylphenyl | 5-quinolyl | 0.61* | 369 |
| 115-18 | 2-trifluoromethylphenyl | 5-isoquinolyl | 0.53* | 369 |
| 115-19 | 2-trifluoromethylphenyl | 2,4-dimethoxy-pyrimidin-5-yl | 0.88* | 380 |
| 115-20 | 2-trifluoromethylphenyl | 1-methylindazol-6-yl | 0.85* | 372 |
| 115-21 | 2-trifluoromethylphenyl | 2,5-dichloro-3-thienyl | 1.16* | 392 |
| 115-22 | 2-trifluoromethylphenyl | 4-isoquinolyl | 0.55* | 369 |
| 115-23 | 2-trifluoromethylphenyl | 1H-indol-4-yl | 0.86* | 357 |
| 115-24 | 2-trifluoromethylphenyl | 5-(trifluoromethyl)-3-pyridyl | 0.92* | 387 |
| 115-25 | 2-trifluoromethylphenyl | 2-cyano-5-methyl-3-furyl | 0.93* | 347 |
| 115-26 | 2-trifluoromethylphenyl | pyrido[2,3-b]pyrazin-7-yl | 0.67* | 371 |
| 115-27 | 2-trifluoromethylphenyl | 4-pyridyl | 0.36* | 319 |
| 115-28 | 2-trifluoromethylphenyl | 3-methylimidazol-4-yl | 0.26* | 322 |
| 115-29 | 2-trifluoromethylphenyl | 8-quinolyl | 1.11* | 369 |
| 115-30 | 2-trifluoromethylphenyl | 2-pyridyl | 0.92** | 319 |
| 115-31 | 2-trifluoromethylphenyl | 3-chloro-2-pyridyl | 1.17** | 353 |
| 115-32 | 2-trifluoromethylphenyl | 5-(trifluoromethyl)-2-pyridyl | 1.18** | 387 |
| 115-33 | 2-trifluoromethylphenyl | 3,5-dichloro-2-pyridyl | 1.04** | 387 |
| 115-34 | 2-trifluoromethylphenyl | 3-chloro-5-trifluoromethyl-2-pyridyl | 1.26** | 421 |

*Method E used
**FFMethod A used

Table 115 shows selected melting point, selected HPLC-MS, and selected NMR data for compounds (IX) of the present invention. CDCl$_3$ was used as the solvent for NMR measurements, unless otherwise stated. No attempt is made to list all characterising data in all cases.

TABLE 116

Compounds of formula (I)

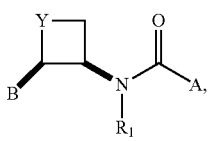

(I)

| Entry | A | B | Y | R1 | RT (min) | [M + H] (measured) | Method | MP (° C.) |
|---|---|---|---|---|---|---|---|---|
| 116-1 | 2-trifluoromethylphenyl | 5-fluoro-pyrid-2-yl | O | H | 0.77 | 341 | A | |
| 116-2 | 3-trifluoromethylpyrid-2-yl | 3-methyl-thien-2-yl | CH2 | H | 1.06 | 341 | A | |
| 116-3 | 3-trifluoromethylpyrid-2-yl | 5-chloro-thien-2-yl | CH2 | H | 1.07 | 361 | A | |
| 116-4 | 2-trifluoromethylphenyl | 3-methyl-thien-2-yl | CH2 | H | | | | 111-112 |
| 116-5 | 2-trifluoromethylphenyl | 5-chloro-thien-2-yl | CH2 | H | | | | 137-138 |
| 116-6 | 2-trifluoromethylpyrid-3-yl | 3-methyl-thien-2-yl | CH2 | H | 0.96 | 341 | A | 148-149 |
| 116-7 | 2-trifluoromethylpyrid-3-yl | 5-chloro-thien-2-yl | CH2 | H | 0.99 | 361 | A | 150-151 |
| 116-8 | 3-trifluoromethylpyrazin-2-yl | 5-chloro-thien-2-yl | CH2 | H | 1.03 | 362 | A | |
| 116-9 | 3-trifluoromethylpyrazin-2-yl | 3-methyl-thien-2-yl | CH2 | H | 1.02 | 342 | A | 123-124 |
| 116-10 | 2-trifluoromethylphenyl | 6-chloro-pyridin-3-yl | CH2 | H | 0.91 | 355 | A | 152-153 |
| 116-11 | 2-trifluoromethylpyrid-3-yl | 6-chloro-pyridin-3-yl | CH2 | H | 0.83 | 356 | A | 166-169 |
| 116-12 | 3-trifluoromethylpyrazin-2-yl | 6-chloro-pyridin-3-yl | CH2 | H | 0.85 | 357 | A | 159-162 |
| 116-13 | 3-chloropyrazin-2-yl | 6-chloro-pyridin-3-yl | CH2 | H | | | | 141-143 |
| 116-14 | 3-trifluoromethylpyrid-2-yl | 6-chloro-pyridin-3-yl | CH2 | H | 0.87 | 356 | A | 134-135 |
| 116-15 | 2-trifluoromethylphenyl | 4-chloro-1-methyl-1H-pyrazol-3-yl | CH2 | H | 0.94 | 358 | A | |
| 116-16 | 2-trifluoromethylpyrid-3-yl | 4-chloro-1-methyl-1H-pyrazol-3-yl | CH2 | H | 0.85 | 359 | A | 121-122 |
| 116-17 | 3-trifluoromethylpyrid-2-yl | 4-chloro-1-methyl-1H-pyrazol-3-yl | CH2 | H | 0.93 | 359 | A | |
| 116-18 | 3-trifluoromethylpyrazin-2-yl | 4-chloro-1-methyl-1H-pyrazol-3-yl | CH2 | H | 0.9 | 360 | A | |

TABLE 116-continued

Compounds of formula (I)

$$\text{(I)}$$

| Entry | A | B | Y | R1 | RT (min) | [M + H] (measured) | Method | MP (° C.) |
|---|---|---|---|---|---|---|---|---|
| 116-19 | 2-trifluoromethylphenyl | 6-trifluoromethyl-pyridin-3-yl | CH2 | H | 0.96 | 389 | | 164-165 |
| 116-20 | 2-trifluoromethylpyrid-3-yl | 6-trifluoromethyl-pyridin-3-yl | CH2 | H | 0.88 | 390 | | 147-148 |
| 116-21 | 3-trifluoromethylpyrazin-2-yl | 6-trifluoromethyl-pyridin-3-yl | CH2 | H | 0.9 | 391 | | 151-153 |
| 116-22 | 3-trifluoromethylpyrid-2-yl | 6-trifluoromethyl-pyridin-3-yl | CH2 | H | 0.93 | 390 | | 155-157 |
| 116-23 | 3-chloropyrazin-2-yl | 6-trifluoromethyl-pyridin-3-yl | CH2 | H | 0.84 | 357 | | 145-146 |
| 116-24 | 2-trifluoromethylphenyl | benzothiophen-2-yl | CH2 | H | 1.74 | 376 | D | |
| 116-25 | 2-trifluoromethylphenyl | thiazol-5-yl | CH2 | H | 1.12 | 327 | D | |
| 116-26 | 2-trifluoromethylphenyl | 4-(trifluoromethyl)-pyridin-3-yl | CH2 | H | 1.39 | 389 | D | |
| 116-27 | 2-trifluoromethylphenyl | pyrimidin-5-yl | CH2 | H | 0.96 | 322 | D | |
| 116-28 | 2-trifluoromethylphenyl | benzofuran-2-yl | CH2 | H | 1.65 | 360 | D | |
| 116-29 | 2-trifluoromethylphenyl | 3-quinolyl | CH2 | H | 1.05 | 371 | D | |
| 116-30 | 2-trifluoromethylphenyl | 5-methylbenzothiophen-2-yl | CH2 | H | 1.85 | 390 | D | |
| 116-31 | 2-trifluoromethylphenyl | 2-methylindazol-5-yl | CH2 | H | 1.27 | 374 | D | |
| 116-32 | 2-trifluoromethylphenyl | 1-methylindazol-5-yl | CH2 | H | 1.39 | 374 | D | |
| 116-33 | 2-trifluoromethylphenyl | 1,3-benzothiazol-5-yl | CH2 | H | 1.39 | 377 | D | |
| 116-34 | 2-trifluoromethylphenyl | 1-methylindol-5-yl | CH2 | H | 1.64 | 373 | D | |
| 116-35 | 2-trifluoromethylphenyl | 1,2,3,4-tetrahydroquinolin-8-yl | CH2 | H | 0.7 | 375 | D | |
| 116-36 | 2-trifluoromethylpyrid-3-yl | 2-(6-bromo-1,3-benzodioxol-5-yl) | CH2 | H | 0.97 | 443 | A | 138-140 |
| 116-37 | 2-trifluoromethylphenyl | 2-(6-bromo-1,3-benzodioxol-5-yl) | CH2 | H | 1.04 | 442 | A | 120-121 |
| 116-38 | 3-chloropyrazin-2-yl | 2-(2,2-difluoro-1,3-benzodioxol-4-yl) | CH2 | H | 0.99 | 366 | A | 92-93 |
| 116-39 | 3-trifluoromethylpyrazin-2-yl | 2-(2,2-difluoro-1,3-benzodioxol-4-yl) | CH2 | H | 1.03 | 402 | A | 103-104 |
| 116-40 | 3-trifluoromethylpyrid-2-yl | 2-(2,2-difluoro-1,3-benzodioxol-4-yl) | CH2 | H | 1.07 | 401 | A | |
| 116-41 | 2-chloropyrid-3-yl | 2-(2,2-difluoro-1,3-benzodioxol-4-yl) | CH2 | H | 0.96 | 367 | A | 120-121 |
| 116-42 | 2-trifluoromethylpyrid-3-yl | 2-(2,2-difluoro-1,3-benzodioxol-4-yl) | CH2 | H | 1.00 | 401 | A | 120-122 |
| 116-43 | 2-trifluoromethylphenyl | 2-(2,2-difluoro-1,3-benzodioxol-4-yl) | CH2 | H | 1.07 | 400 | A | 93-94 |
| 116-44 | 2-trifluoromethylphenyl | 5-quinolyl | CH2 | H | 1.11 | 371 | D | |
| 116-45 | 2-trifluoromethylphenyl | 2,5-dichloro-3-thienyl | CH2 | H | 1.9 | 394 | D | |
| 116-46 | 2-trifluoromethylphenyl | 1H-indol-4-yl | CH2 | H | 1.59 | 359 | D | |
| 116-47 | 2-trifluoromethylphenyl | 5-(trifluoromethyl)-3-pyridyl | CH2 | H | 1.54 | 389 | D | |
| 116-48 | 2-trifluoromethylphenyl | 8-quinolyl | CH2 | H | 1.3 | 371 | D | |
| 116-49 | 2-trifluoromethylphenyl | 2-pyridyl | CH2 | H | 1 | 321 | D | |
| 116-50 | 2-trifluoromethylphenyl | 3-chloro-2-pyridyl | CH2 | H | 0.97 | 355 | A | |
| 116-51 | 2-trifluoromethylphenyl | 5-(trifluoromethyl)-2-pyridyl | CH2 | H | 1 | 389 | A | |
| 116-52 | 2-trifluoromethylphenyl | 5-chloro-2-furyl | CH2 | H | | | | 117-118 |
| 116-53 | 2-trifluoromethylphenyl | 5-bromo-2-furyl | CH2 | H | | | | 90-92 |
| 116-54 | 2-trifluoromethylpyrid-3-yl | 5-bromo-2-furyl | CH2 | H | | | | 87-89 |
| 116-55 | 3-trifluoromethylpyrid-2-yl | 5-bromo-2-furyl | CH2 | H | 0.99 | 389 | A | |
| 116-56 | 3-trifluoromethylpyrazin-2-yl | 5-bromo-2-furyl | CH2 | H | 0.96 | 390 | A | |
| 116-57 | 2-chloropyrid-3-yl | 5-bromo-2-furyl | CH2 | H | | | | 81-82 |
| 116-58 | 3-chloropyrazin-2-yl | 5-bromo-2-furyl | CH2 | H | 0.9 | 356 | A | |
| 116-59 | 2,6-difluoro-phenyl | 5-bromo-2-furyl | CH2 | H | | | | 89-91 |
| 116-60 | 3-chloropyrid-2-yl | 5-bromo-2-furyl | CH2 | H | 0.94 | 355 | A | |
| 116-61 | 2-trifluoromethylphenyl | 3,5-dichloro-2-pyridyl | CH2 | H | 0.96 | 389 | A | |

Table 116 shows selected melting point, selected HPLC-MS, and selected NMR data for compounds(I) of the present invention. CDCl$_3$ was used as tl solvent for NMR measurements, unless otherwise stated. No attempt is made to list all characterising data in all cases.

TABLE 117

Trans isomers of (I)

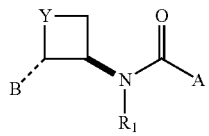

Trans isomers of (I)

| Entry | A | B | Y | R1 | RT (min) | [M + H] (meas-ured) | MP (° C.) |
|---|---|---|---|---|---|---|---|
| 117-1 | 2-trifluoromethyl phenyl | 2-(6-bromo-1,3-benzodioxol-5-yl) | CH2 | H | 1.07* | 442 | 145-146 |

*Method A

Table 117 shows selected melting point, selected HPLC-MS for trans isomers of compounds (I) of the present invention. No attempt is made to list all characterising data in all cases.

RT refers to the retention time of the HPLC-MS method and RT' refers to the retention time of the desired enantiomer in the chiral HPLC method

TABLE 118

Compounds of formula (Iab)

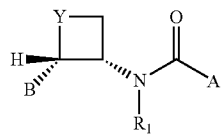

(Iab)
abolute stereochenistry

| Entry | A | B | Y | R1 | RT (min) | [M + H] (meas-ured) | RT' (min) | Chiral Method |
|---|---|---|---|---|---|---|---|---|
| 118-1 | 2-trifluoro-methyl-pyrid-3-yl | 5-chloro-thien-2-yl | CH2 | H | 0.99* | 361 | 3.90 | B |
| 118-2 | 2-trifluoro-methylphenyl | 3-chloro-2-pyridyl | CH2 | H | 0.97* | 355 | 4.66 | F |
| 118-3 | 2-trifluoro-methylphenyl | 5-fluoro-2-pyridyl | O | H | 0.77* | 341 | 5.52 | G |

*Method A

Table 118 shows selected melting point, selected HPLC-MS for compounds of the present invention. No attempt is made to list all characterising data in all cases.

RT refers to the retention time of the HPLC-MS method and RT' refers to the retention time of the desired enantiomer in the chiral HPLC method. Compounds 118-1 and 118-3 were obtained through the resolution of racemates via preparative chiral HPLC.

Method A

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

Method B (Chiral)

Waters UPLC—HClass from Waters: solvent degasser, quaternary pump and PDA detector Column: Chiralpak IC, length (mm) 100, internal diameter (mm) 4.6, particle size (p) 3, wavelength (nm): 240 nm, solvent: Isocratic Heptane: EtOH 80:20, injection volume 2 µl, flow (ml/min) 1.0

Method C (GC-MS)

GC-MS was conducted on a Thermo, MS: ISQ and GC: TRACE GC ULTRA with a column from Zebron phenomenex: Phase ZB-5 ms 15 m, diam: 0.25 mm, 0.25 µm, H$_2$ flow 1.7 ml/min, temp injector: 250° C., temp detector: 220° C., method: start at 70° C., 25° C./min until 320° C., hold 2 min at 320° C., total time 12 min.

CI reagent gas: Methane, flow 1 ml/min

Method D

ACQUITY SQD Mass Spectrometer from Waters (Single quadrupole mass spectrometer)

Ionisation method: Electrospray

Polarity: positive ions

Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method E

ACQUITY SQD Mass Spectrometer from Waters (Single quadrupole mass spectrometer)

Ionisation method: Electrospray

Polarity: positive ions

Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 80 | 20 | 1 |
| 0.1 | 75 | 25 | 1 |
| 0.2 | 70 | 30 | 0.75 |
| 1.2 | 0 | 100 | 0.75 |
| 1.40 | 0 | 100 | 0.75 |
| 1.45 | 80 | 20 | 1 |

Type of column: Waters ACQUITY UPLC HSS T3; Column length: 30 mm; Internal diameter of column: 2.1 mm; Particle Size: 1.8 micron; Temperature: 60° C.

Method F (Chiral)

Waters UPLC—HClass from Waters: solvent degasser, quaternary pump and PDA detector Column: Chiralpak IC, length (mm) 100, internal diameter (mm) 4.6, particle size (p) 3, wavelength (nm): 272 nm, solvent: Isocratic Heptane: iPrOH 80:20, injection volume 2 μl, flow (ml/min) 1.0

Method G (Chiral)

Waters UPLC—HClass from Waters: solvent degasser, quaternary pump and PDA detector Column: Chiralpak IC, length (mm) 100, internal diameter (mm) 4.6, particle size (p) 3, wavelength (nm): 265 nm, solvent: Isocratic Heptane: iPrOH 70:30, injection volume 2 μl, flow (ml/min) 1.0

BIOLOGICAL EXAMPLES

*Meloidogyne* Spp. (Root-Knot Nematode)

Nematicide, Contact Activity, Preventive.

Filter papers (9 cm×4.5 cm) with a small pocket were placed into plastic pouches (12 cm×6 cm). One cucumber cv. Toshka seed was placed in the centre of the filter paper pocket of all the pouches needed for a test. The cucumber seeds in the pouches were treated with test solutions at 200 ppm by pipetting the solution directly over the cucumber seed in the filter paper pocket in the pouch. Prior to application, the compound solution was prepared at twice the concentration required and the egg suspension is prepared with FORL nutrient solution with 3000 eggs/0.5 ml. After applying all the treatments, 3000 eggs (in 0.5 ml of FORL nutrient solution) were pipetted into the pouches. The pouches were incubated in a moist chamber for twelve days and watered regularly to maintain good filter paper moisture essential for the growing cucumber root system. After this period, the filter paper containing the germinated cucumber seedling was removed from the plastic pouch to assess the number of galls caused by *Meloidogyne* spp. per root system.

The following compounds showed a greater than 80% reduction of galling compared to the untreated control: 116-2, 116-3, 116-5, 116-6, 116-7, 116-8, 116-9, 116-10, 116-11, 116-12, 116-13, 116-14, 116-20, 116-21, 116-22, 116-23.

*Heterodera schachtii* (Sugar beet cyst nematode), Nematicide, contact activity

The tested application rate of each compound was 20 ppm. All solutions were brought to a concentration of 40 ppm, respectively, as they were subsequently diluted by adding the equivalent amount of water containing juvenile nematodes. After preparation of the suspensions, 1 ml of each suspension and concentration was transferred to 16-well assay plates with a total of three replicates per treatment. Approximately 500 juveniles of *Heterodera schachtii* were added in 1 ml of water to each well. Nematodes in water served as controls. The plates were placed in a dark box and stored at room temperature. Nematode paralysis was determined after 24 hours incubation at 25° C. in darkness. Nematodes that showed no movement were considered immotile.

The following compounds showed a greater than 75% nematode immobilization compared to the untreated control: 116-2, 116-3, 116-4, 116-6, 116-7, 116-8, 116-9, 116-10, 116-11, 116-12, 116-13, 116-14, 116-17, 116-19, 116-21, 116-22, 116-26, 116-35, 116-48, 116-50, 116-51, 118-1, 118-2.

*Meloidogyne* Spp. (Root-Knot Nematode)

Nematicide, contact activity, preventive

Cucumber cv. Toshka seeds were sown directly into pots filled with a sandy substrate. Six days later pots were each treated with 5 ml of a WP10 suspension of the test compound. Hereafter, pots were inoculated with 3000 eggs of *M. incognita*. The trial was harvested fourteen days after trial application and inoculation. Root galling was assessed according to Zeck's gall index (Zeck W. M. (1971) Ein Bonitierungsschema zur Feldauswertung von Wurzelgallenbefall. Pflanzenschutznachrichten Bayer 24, 1: 144-147.). The following compounds showed a greater than 80% reduction of galling compared to the untreated control: 116-3, 116-4, 116-5, 116-6, 116-7, 116-8, 116-10, 116-11, 116-12, 116-13, 116-14, 116-15, 116-16, 116-19, 116-21, 116-22, 116-23, 116-40, 116-42.

*C. elegans* In-Vivo Assay:

*C. elegans* were cultured using standard conditions as described in "The nematode *Caenorhabditis elegans*" (W. B. Wood, Cold Spring Harbor Laboratory Press 1988). Eggs from a drug hypersensitive *C. elegans* mutant strain were isolated. Eggs were placed on solutions of test compounds at a concentration of 50 ppm. Tests were conducted in duplicate. Eggs were incubated at 25° C. for 72 hours. Development of eggs was assessed visually after 72 hours and recorded photographically.

The following compounds showed a total inhibition of egg development: 118-3.

The invention claimed is:

1. A compound of the formula I:

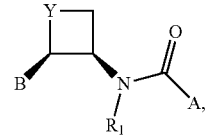

wherein:
Y represents O or $CH_2$;
A is phenyl, wherein the phenyl is optionally substituted by one or more $R_2$;
B is pyrid-2-yl, thien-2-yl, pyrid-3-yl, pyrazol-3-yl, benzothiophen-2-yl, thiazol-5-yl, pyrimidin-5-yl, benzofuran-2-yl, quinol-3-yl, benzothiophen-2-yl, indazol-5-yl, benzothiazol-5-yl, indol-5-yl, 1,2,3,4-tetrahydroquinolin-8-yl, benzodioxol-5-yl, benzodioxol-4-yl, quinol-5-yl, thien-3-yl, or indol-4-yl, quinol-8-yl; each optionally substituted by one or more $R_4$;

$R_1$ is hydrogen, $C_1$-$C_4$-alkyl, $C_1$-$C_4$-alkoxycarbonyl, $C_2$-$C_4$-alkenyl, $C_2$-$C_4$-alkynyl, $C_1$-$C_4$-cyanoalkyl or $C_3$-$C_6$-cycloalkylcarbonyl, $C_3$-$C_6$-cycloalkoxycarbonyl or benzyl;

each $R_2$ independently of one another represent halogen, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-haloalkylthio;

each $R_4$ independently of one another represent halogen, cyano, $C_1$-$C_4$-alkyl, $C_1$-$C_4$-haloalkyl, $C_1$-$C_4$-alkoxy, $C_1$-$C_4$-haloalkoxy, $C_2$-$C_6$-haloalkenyl, $C_2$-$C_6$ haloalkynyl or $C_3$-$C_6$-cycloalkyl optionally substituted by one or more substituents $R_5$;

each $R_5$ independently of one another represent halogen, cyano, $C_1$-$C_4$-alkyl, $C_1$-$C_4$-haloalkyl or $C_1$-$C_4$-alkyloxycarbonyl;

or an enantiomer, a salt or an N-oxide of the compound.

2. A compound according to claim 1, wherein $R_1$ is hydrogen.

3. A compound of formula (I) according to claim 1 wherein:

Y represents O or $CH_2$;

$R_1$ is hydrogen;

each $R_2$ independently of one another represent halogen, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-haloalkylthio;

each $R_4$ independently of one another represent halogen, cyano, $C_1$-$C_4$-haloalkyl, $C_1$-$C_4$-haloalkoxy or $C_3$-$C_6$-cycloalkyl optionally substituted by one or more substituents $R_5$;

each $R_5$ independently of one another represent selected from halogen, $C_1$-$C_4$-alkyl or $C_1$-$C_4$-haloalkyl.

4. A compound of formula (I) according to claim 1 wherein:

Y is $CH_2$;

A represents phenyl wherein the phenyl is optionally substituted by one or more $R_2$;

$R_1$ is hydrogen;

each $R_2$ independently of one another represent halogen, difluoromethyl or trifluoromethyl;

each $R_4$ independently of one another represent halogen or trifluoromethyl.

5. A compound of formula (I) according to claim 1 wherein:

Y represents $CH_2$;

A represents phenyl optionally substituted by one or more $R_2$;

$R_1$ represents hydrogen;

each $R_2$ independently of one another represent halogen, difluoromethyl or trifluoromethyl;

each $R_4$ independently of one another represent halogen or trifluoromethyl.

6. A compound of formula (Iab):

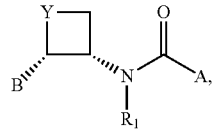

wherein Y, A, B, and $R_1$ are as defined in claim 1.

7. A pesticidal composition, which, in addition to comprising formulation adjuvants, comprises a nematicidal effective amount of a compound of the formula (I) according to claim 1.

8. A composition according to claim 7, which further comprises one or more insecticidally, acaricidally, nematicidally and/or fungicidally active agents.

* * * * *

UNITED STATES PATENT AND TRADEMARK OFFICE
CERTIFICATE OF CORRECTION

PATENT NO. : 10,207,985 B2
APPLICATION NO. : 14/908239
DATED : February 19, 2019
INVENTOR(S) : Regis Jean Georges Mondiere et al.

It is certified that error appears in the above-identified patent and that said Letters Patent is hereby corrected as shown below:

On the Title Page

Item (72), please correct the spelling of the inventor to read as Anthony Cornelius O'Sullivan.

Signed and Sealed this
Twenty-seventh Day of August, 2019

Andrei Iancu
*Director of the United States Patent and Trademark Office*